(12) United States Patent
Fleischman et al.

(10) Patent No.: US 6,994,672 B2
(45) Date of Patent: Feb. 7, 2006

(54) APPARATUS AND METHOD FOR MEASURING INTRAOCULAR PRESSURE

(75) Inventors: Aaron J. Fleischman, University Heights, OH (US); Shuvo Roy, Cleveland, OH (US)

(73) Assignee: Cleveland Clinic Foundation, Cleveland, OH (US)

( * ) Notice: Subject to any disclaimer, the term of this patent is extended or adjusted under 35 U.S.C. 154(b) by 323 days.

(21) Appl. No.: 10/118,440

(22) Filed: Apr. 8, 2002

(65) Prior Publication Data

US 2002/0177768 A1  Nov. 28, 2002

Related U.S. Application Data

(63) Continuation-in-part of application No. 09/642,573, filed on Aug. 21, 2000, now Pat. No. 6,447,449.

(51) Int. Cl.
*A61B 3/16* (2006.01)

(52) U.S. Cl. .................................. 600/406; 600/405
(58) Field of Classification Search ............... 600/398, 600/399, 402, 405, 406
See application file for complete search history.

(56) References Cited

U.S. PATENT DOCUMENTS

| | | | |
|---|---|---|---|
| 4,089,329 A | 5/1978 | Couvillon, Jr. et al. | |
| 4,305,399 A | 12/1981 | Beale | |
| 4,628,938 A | 12/1986 | Lee | |
| 4,922,913 A | 5/1990 | Waters, Jr. et al. | |
| 4,987,898 A * | 1/1991 | Sones | 600/398 |
| 5,005,577 A | 4/1991 | Frenkel | |
| 5,076,274 A | 12/1991 | Matsumoto | |
| 5,109,852 A | 5/1992 | Kaye et al. | |
| 5,165,409 A | 11/1992 | Coan | |
| 5,179,953 A | 1/1993 | Kursar | |
| 5,217,015 A | 6/1993 | Kaye et al. | |
| 5,375,595 A | 12/1994 | Sinha et al. | |
| 5,636,635 A | 6/1997 | Massie et al. | |
| 5,830,139 A * | 11/1998 | Abreu | 600/405 |
| 6,120,460 A | 9/2000 | Abreu | |
| 6,123,668 A | 9/2000 | Abreu | |
| 6,213,943 B1 | 4/2001 | Abreu | |
| 6,287,256 B1 * | 9/2001 | Park et al. | 600/398 |
| 6,579,235 B1 * | 6/2003 | Abita et al. | 600/398 |

OTHER PUBLICATIONS

Pending U.S. Fleishman et al. U.S. Appl. No. 09/642,573, filed Aug. 21, 2000 entitled System for Measuring Intraocular Pressure of an Eye and a MEM Sensor for Use Therewith.

(Continued)

*Primary Examiner*—Max F. Hindenburg
*Assistant Examiner*—Jonathan Foreman
(74) *Attorney, Agent, or Firm*—Tarolli, Sundheim, Covell & Tummino L.L.P.

(57) ABSTRACT

An apparatus (176) for measuring intraocular pressure (IOP) comprises an applanation tonometer (180) having a distal end that is movable toward the eye and a disposable module (188) positioned at the distal end. The module (188) includes a sensor carrier (192) and a sensor (10) connected to the sensor carrier. The sensor (10) comprises a contact surface (14) for making contact with a surface portion of the eye (36). The contact surface (14) includes an outer non-compliant region (16) and an inner compliant region (18) fabricated as an impedance element that varies in impedance as the inner compliant region changes shape. The sensor (10) further comprises a region of conductive material (38) electrically coupled to the impedance element of the compliant region (18) and responsive to an external signal for energizing the impedance element so that the IOP may be determined.

46 Claims, 17 Drawing Sheets

OTHER PUBLICATIONS

Intraocular Pressure Measurement With Instrumented Contact Lenses, Investigative Ophthalmology Report; M. E. Greene, et al.; Apr. 1974, pp. 229-302.

Self-Tonometry to Manage Patients With Glaucoma and Apparently Controlled Intraocular Pressure, J. T. Wilensky, M.D., et al; Arch Ophthamol, vol. 105, Aug. 1987, pp. 1072-1075.

Passive Radiotelemetry of Intraocular Pressure in Vivo: Calibration and Validation of Continual Scleral Guard-Ring Applanation Transensors in the Dog and Rabbit, R. L. Cooper et al.; Assoc. for Res. in Vis. and Ophthal., Inc., vol. 18, No. 9, Sep. 1979, pp. 930-938.

Continual Monitoring of Intraocular Pressure: Effect of Central Venous Pressure, Respiration, and Eye Movements on Continual Recordings of Intraocular Pressure in the Rabbit, Dog, and Man; R. L. Cooper et al.; British Journal of Ophthalmology, vol. 63, 1979, pp. 799-804.

Radio Telemetry of Intraocular Pressure in Vitro; Cooper et al., Invest. Ophthalmol. Visual Sci. Feb. 1977, pp. 168-171.

Progress in Continual Eye Pressure Monitoring; Cooper et al.; Australian Journal of Ophthalmology, vol. 11, 1983 pp. 143-148.

A New Tonometer Based on the Application of Micromechanical Sensors, Besten et al.; Mesa Research Institute, The Netherlands, 1993, pp. 105-110.

Corneal Bending and Buckling in Tonometry, Marg, Ph.D.; et al.; Archives of Ophthalmology, vol. 4, Jan. 1961, pp. 67-74.

Wireless Micromachined Ceramic Pressure Sensors, Jennifer M. English et al.; School of Electrical and Computer Engineering, Georgia Institute of Technology, IEEE, 1999, pp. 511-516.

Dynamic Tonometry, H. M. Dekking et al.; Ophthalmologica, vol. 154, 1967, pp. 59-75.

A Rapid Pneumatic Applanation Tonometer, Maurice E. Langham, Ph.D. et al.; Arch Ophthal, vol. 79, Apr. 1968, pp. 389-399.

The Validity of the Imbert-Fick Law As Applied to Applanation Tonometry, J. Gloster et al.; Exp. Eye Res., vol. 2, May 1963, pp. 274.283.

The Goldmann Applanation Tonometer, Robert A. Moses, M.D.; pp. 865,869 (Undated).

Magnetic Microactuation of Polysiclion Flexure Structures, Jack W. Judy et al.; 1994, pp. 43-59.

A Theoretical and Experimental Study of the Mechanical Behavior of the Cornea With Application to the Measurement of Intraocular Pressure, Nathan Jay Schwartz et al.; University of California, Berkeley, Bulletin of Mathematical Biophysics, vol. 28, 1966, pp. 585-643.

Intraocular Pressure Changes in Patients With Glaucoma, Moore et al. Moorfields Eye Hospital, London, England, pp. 833-835.

Reliability of Intraocular Pressure Measurements After Myopic Excimer Photorefractive Keratectomy, Abbasoglu, M.D., et al.; Ophthalmology, vol. 105, No. 12, Dec. 1998 rev. pp. 2193-2196.

Sources of Error With Use of Goldmann-Type Tonometers, Marc M. Whitacre, M.D., et al.; Survey of Ophthamology, vol. 38, No. 1, Jul.-Aug. 1993, pp. 1-30.

A Noncontact Applanation Tonometer, Max Forbes, M.D., et al.; Arch Ophthalmol, vol. 91, Feb. 1974, pp. 134-140.

Intraocular Pressure and Tonometry, Edwin M. Schottenstein; Clinical Measurements, Chap. 20, pp. 407-428 (Undated).

Trough Height, Pressure and Flattening in Tonometry, Elwin Marg et al.; Vision Research, vol. 1, 1962, pp. 379-385.

Fast, Automatic, Electronic Tonometers Based on an Exact Theory, R. Stuart Mackay, Ph.D. et al.; Acta Ophthalmologica, vol. 37, 1959, pp. 495.507.

A New Technique for in Vivo Intraocular Pharmacokinetic Measurements, Ocular Dialysis, Joshua Ben-Nun, M.D., et al.; Arch. Ophthalmol., vol. 106, Feb. 1988, pp. 254-259.

Diurnal Variation in Intraocular Pressure, Charles D. Phelps, M.D. et al.; American Journal of Ophthalmology, Mar. 1974, pp. 367-376.

A Universal Electromagnetic Microactuator Using Magnetic Interconnection Concepts, Daniel J. Sadler et al.; Journal of Microelectromechanical Systems, vol. 9, No. 4, Dec. 2000, pp. 460-468.

Miniature Passive Pressure Transensor for Implanting in the Eye, Carter C. Collins, IEEE Transactions on Bio-Medical Engineering, vol. BME 14, No. 2, Apr. 1967, pp. 74-83.

* cited by examiner

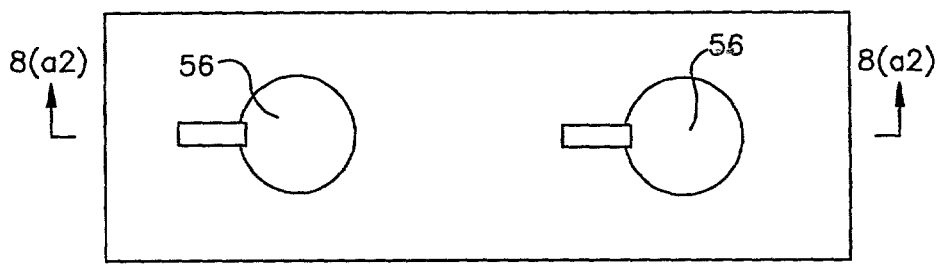
Fig.8(a1)
Fig.8(a2)
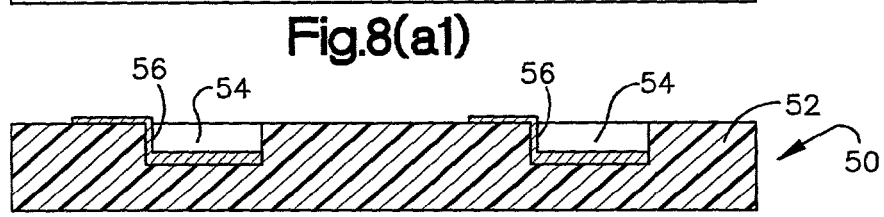
Fig.8(b1)
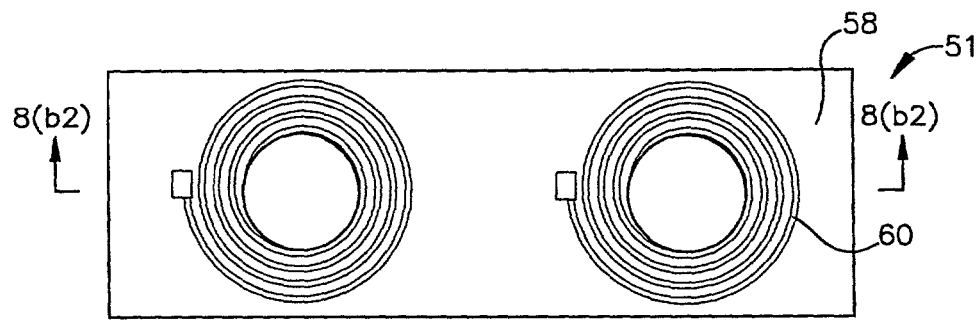
Fig.8(b2)
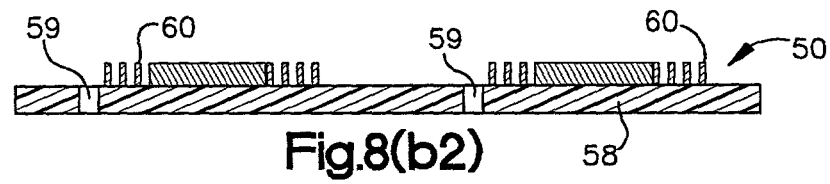
Fig.8(c)
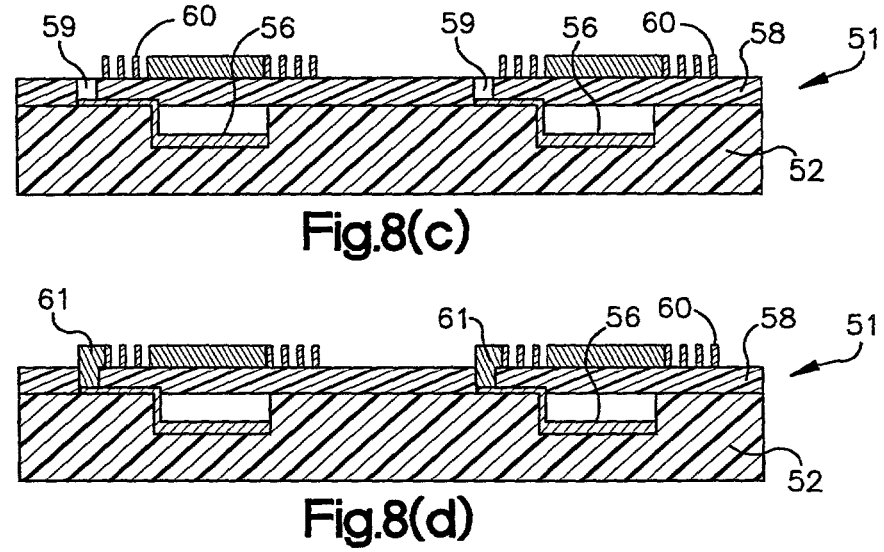
Fig.8(d)

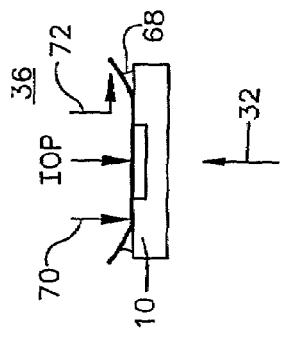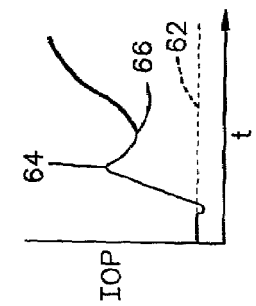
Fig.11(A1) Fig.11(A2)
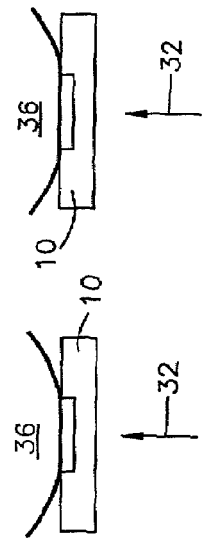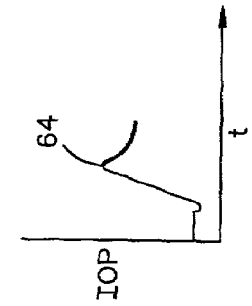
Fig.11(B1) Fig.11(B2)
Fig.11(C1) Fig.11(C2)
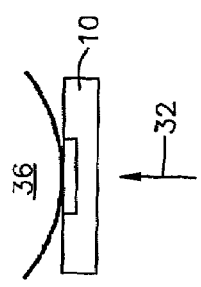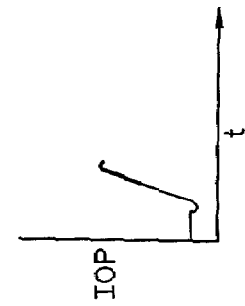
Fig.11(D1) Fig.11(D2)
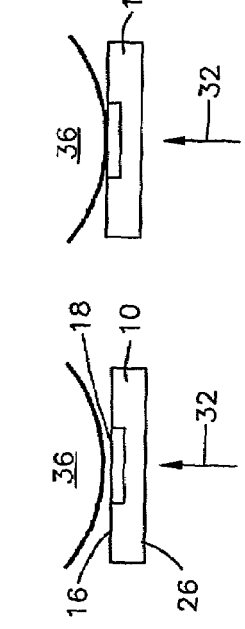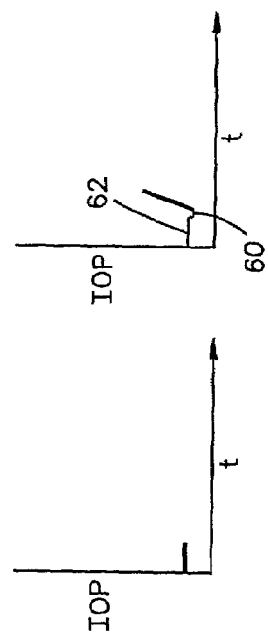
Fig.11(E1) Fig.11(E2)

US 6,994,672 B2

APPARATUS AND METHOD FOR MEASURING INTRAOCULAR PRESSURE

RELATED APPLICATIONS

This application is a continuation-in-part of a co-pending U.S. patent application Ser. No. 09/642,573, entitled "SYSTEM FOR MEASURING INTRAOCULAR PRESSURE FOR AN EYE AND A MEM SENSOR FOR USE THEREWITH", filed Aug. 21, 2000 now U.S. Pat. No. 6,447,449. The subject matter of the aforementioned co-pending application is incorporated herein by reference.

FIELD OF THE INVENTION

The present invention relates to an apparatus and method for measuring intraocular pressure in an eye, and is particularly directed to an apparatus and method that utilize microelectromechanical systems (MEMS) technology to measure intraocular pressure.

BACKGROUND OF THE INVENTION

The measurement of intraocular pressure (IOP) is a routine part of an eye exam. IOP is also monitored closely following certain surgical procedures on the eye. IOP of an eye is typically measured using an applanation tonometer mounted on a slit lamp biomicroscope. Before using the applanation tonometer, an anesthetic and a dye, such as fluorescein, are placed in the eye.

When a cobalt blue filter is put on a light source shined into the eye, the fluorescein dye glows a bright green. The doctor (or technician) then looks through the tonometer and turns a dial until the tonometer tip flattens a given amount of the corneal surface of the eye. The amount of IOP is calculated using the relationship between (i) the force required to flatten the cornea (in mmHg) and (2) the area of cornea flattened. During this process, the tonometer tip, which is usually a plastic part or a glass prism that has been disinfected with an alcohol wipe, touches the front of the cornea. It is desirable to provide an apparatus for measuring IOP in which the tip of the tonometer includes a disposable, and thus extremely sanitary, pressure sensor.

SUMMARY OF THE INVENTION

The present invention is an apparatus for measuring intraocular pressure of an eye. The apparatus comprises an applanation tonometer having a distal end that is movable toward the eye and a disposable module positioned at the distal end of the applanation tonometer. The module includes a sensor carrier and a sensor connected to the sensor carrier. The sensor comprises a contact surface for making contact with a surface portion of the eye. The contact surface includes an outer non-compliant region and an inner compliant region fabricated as an impedance element that varies in impedance as the inner compliant region changes shape. The sensor further comprises a region of conductive material that is electrically coupled to the impedance element of the compliant region and responsive to an external signal for energizing the impedance element so that the intraocular pressure may be determined.

The present invention also provides a method for measuring intraocular pressure (IOP) of an eye. According to the inventive method, an applanation tonometer is provided with a distal end that is movable toward the eye. A disposable module is positioned at the distal end of the applanation tonometer. The module includes a sensor carrier and a sensor connected to the carrier. The sensor has a compliant region that functions as an impedance element. The distal end of the applanation tonometer is moved until the sensor comes into contact with a surface portion of the eye which causes the compliant region to change shape and vary in impedance. The impedance element is energized and a representative pressure measurement is determined each time the impedance element is energized. The representative pressure measurements are processed to render a resultant IOP measurement.

BRIEF DESCRIPTION OF THE DRAWINGS

The foregoing and other features of the present invention will become apparent to those skilled in the art to which the present invention relates upon reading the following description with reference to the accompanying drawings, in which:

FIGS. 8($a$1)–8($d$) are cross-sectional and plan views of another alternate tonometer sensor through various stages of a fabrication process;

FIGS. 11A1–11E2 are illustrations of the response of the apparatus of FIG. 9 to contact with an eye;

DETAILED DESCRIPTION OF EMBODIMENTS

Figure 1:
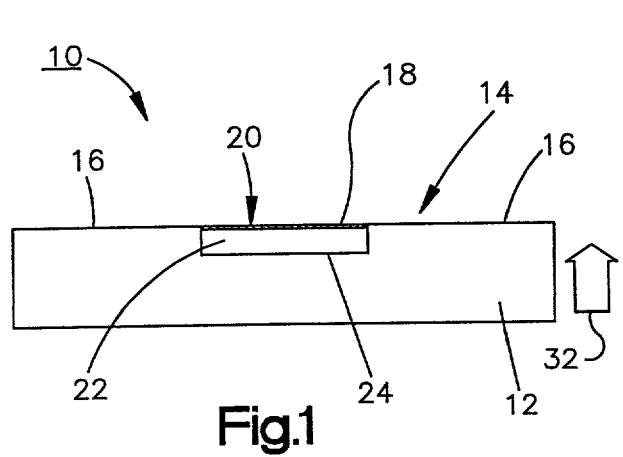
FIG. 1 is a cross-sectional view of a first embodiment of a tonometer sensor for use in the present invention.
Figure 2:
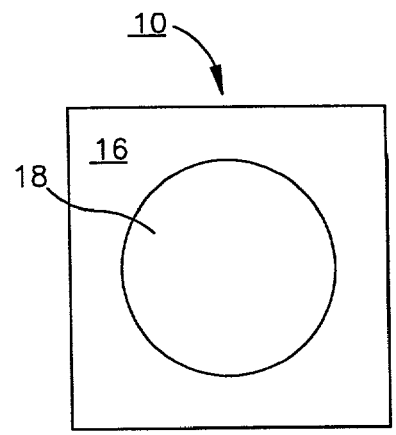
FIG. 2 is a plan view of the tonometer sensor of FIG. 1.

A tonometer sensor 10 produced using microelectromechanical system (MEMS) techniques is shown in FIGS. 1 and 2. The tonometer sensor 10 includes a substrate 12 that is comprised of a silicon material, but it should be understood that other materials may be used. The substrate 12 includes a contact surface 14 for making contact with a surface portion 34 (FIG. 3A) of an eye 36. The surface 14 includes an outer non-compliant region 16 (FIG. 1) and an inner compliant region 18 that is fabricated using MEMS techniques (which will be described in greater detail herein below) as an impedance element, the impedance of which varies as the inner compliant region 18 changes shape. The compliant region 18 comprises a diaphragm 20 as one plate of a capacitive element that is separated by a dielectric 22 from another plate 24 of the capacitive element which is part of the non-compliant region 16. As will become more evident from the description below, as the contact surface 14 is pressed against the surface portion of the eye, the diaphragm plate 20 flexes closer to the other non-compliant plate 24 to change the capacitance of the capacitive element in proportion to the intraocular pressure (IOP) of the eye. In the illustrated embodiment, the dielectric comprises air, but other suitably compliant dielectrics such as hydrogel and silicone, for example, may also be used, without deviating from the principles of the present invention.

Figure 3A:
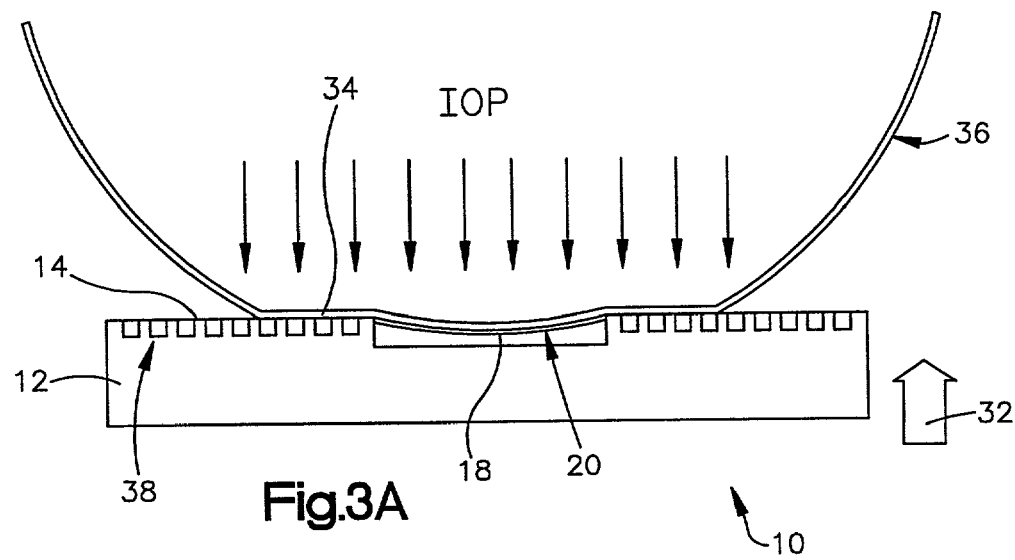
FIGS. 3A and 3B are cross-sectional and plan views, respectively, of the tonometer sensor illustrating additional regions in accordance with the present invention.
Figure 3B:
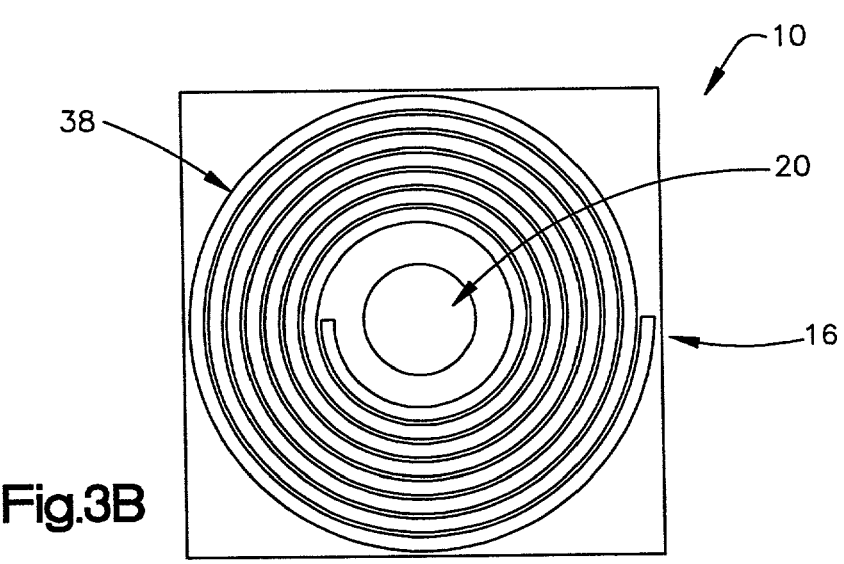

As shown by the substrate cross-sectional and plan views of FIGS. 3A and 3B, respectively, a region of conductive material 38 is included as part of the substrate 12 and is electrically coupled to the impedance element of the compliant region 18 (diaphragm 20) which is a capacitive element. While not shown in FIGS. 3A and 3B, this electrical coupling is described in greater detail in connection with the fabrication drawings found herein below. The conductive material 38 is responsive to an external signal for energizing the impedance element so that the IOP may be determined. In FIGS. 3A and 3B, the conductive region 38 comprises an inductor coil fabricated in the non-compliant region 16 of the contact surface 14 such that it is electrically coupled to the capacitive element to form a resonance or tank circuit. It should be understood that other types of sensors (piezoelectric, piezoresistive, strain-gage based, etc.) could be substituted for the sensor 10. Such other types of sensors would likely require use of other known telemetry techniques rather than a tank circuit.

Figure 4A:
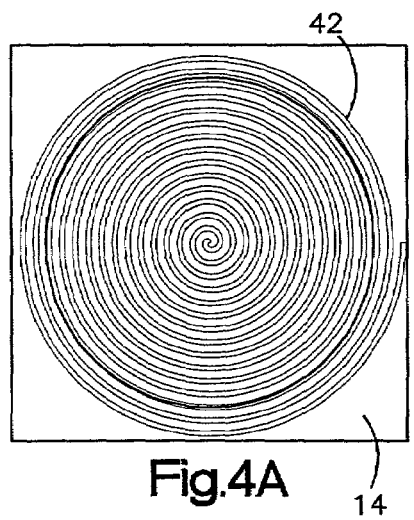
FIGS. 4A and 4B are cross-sectional and plan views, respectively, of a tonometer sensor constructed in accordance with an alternate embodiment of the present invention.
Figure 4B:
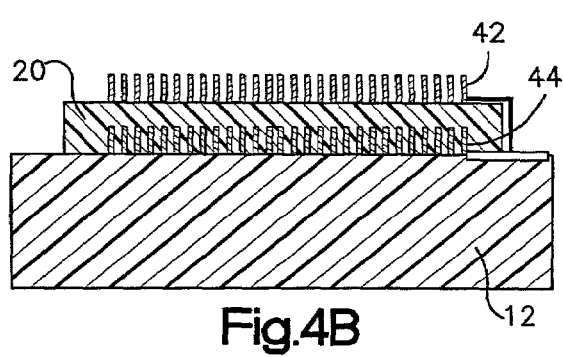

In the present embodiment, the inductor coil 38 is formed by disposing conductive material in a predetermined pattern, like a concentric spiraled pattern, for example, in the non-compliant region 16. A process for fabricating the inductor coil 38 at the non-compliant region 16 is described in greater detail herein below. However, it should be understood that the inductor region need not be embodied solely at the non-compliant region 16 and may be embodied as part of the compliant region 18 as well without deviating from the principles of the present invention. Further, it should be understood by those of ordinary skill in the art that there could be a spiral inductor 42 on the contact surface 14 of the diaphragm 20 coupled to a flat spiral inductor 44 underneath the diaphragm as illustrated in the alternate embodiment of FIGS. 4A and 4B. Yet another alternative would include a combination of the aforementioned spiral inductor 42 and the capacitive element, formed by the diaphragm (plate) 20 and the fixed plate 24, acting in conjunction with each other, meaning the inductance and the capacitance will increase (as the plates get closer to each other) or decrease together.

In the present embodiment, the resonant circuit comprising the inductor coil 38 and the capacitive element formed by the plates 20 and 24 may be excited into resonance by an external electromagnetic signal in the radio frequency (RF) range. Tank circuits of this type have a natural resonant frequency fo that, to the first order, depends of the values of the inductor and the capacitor as follows:

$$fo = 1/2\pi (LC)^{1/2}$$

where L is the inductance and C is the capacitance. Accordingly, as the capacitance of the tonometer sensor 10 changes, the resonant frequency fo of the tank circuit will change in proportion thereto.

For example, if the contact area 14 of the tonometer sensor 10 is approximately one square millimeter (1 mm$^2$) or one millimeter (1 mm) on each side, the diaphragm 20 of the compliant region 18 may have a diameter of five hundred micrometers (500 $\mu$m) with a one and a half micrometer (1.5 $\mu$m) dielectric or air gap, and the inductor coil may have twenty-five (25) turns with an inside diameter (ID) of five hundred micrometers (500 $\mu$m) and an outside diameter (OD) of one thousand micrometers (1,000 $\mu$m). With the diaphragm 20 undisturbed, the resonant frequency may be on the order of one hundred and ninety-three megahertz (193 MHz). Accordingly, a ten percent (10%) increase in capacitance, for example, resulting from a diaphragm 20 deflection will produce a downward shift in resonant frequency to one hundred and eighty-four point one megahertz (184.1 MHz) and this shift in resonant frequency is readily discernible electronically as will be further described herein below. It is understood that the contact area of the sensor 10 may be less than 1 mm, in which case the various dimensions may be rescaled proportionately.

Figure 5A:
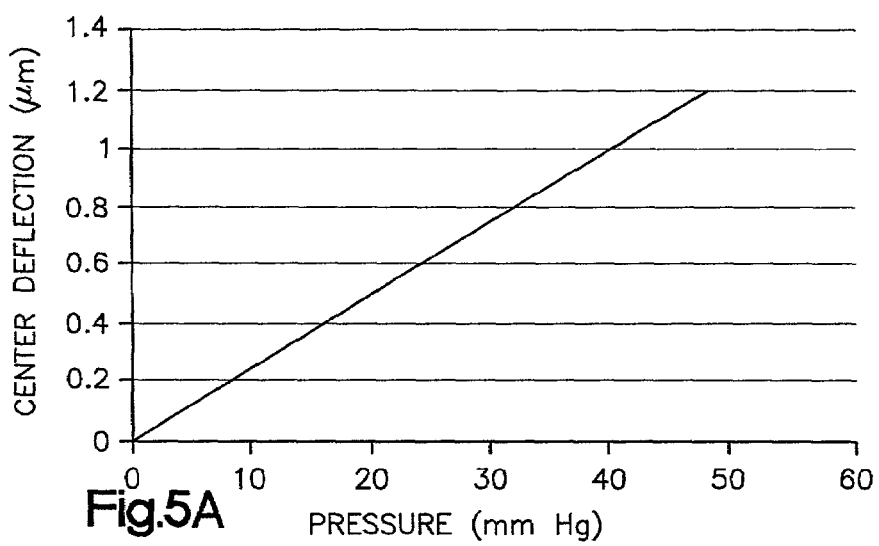
FIG. 5A is a graph illustrating the relationship between deflection of the tonometer sensor and intraocular pressure (IOP)
Figure 5B:
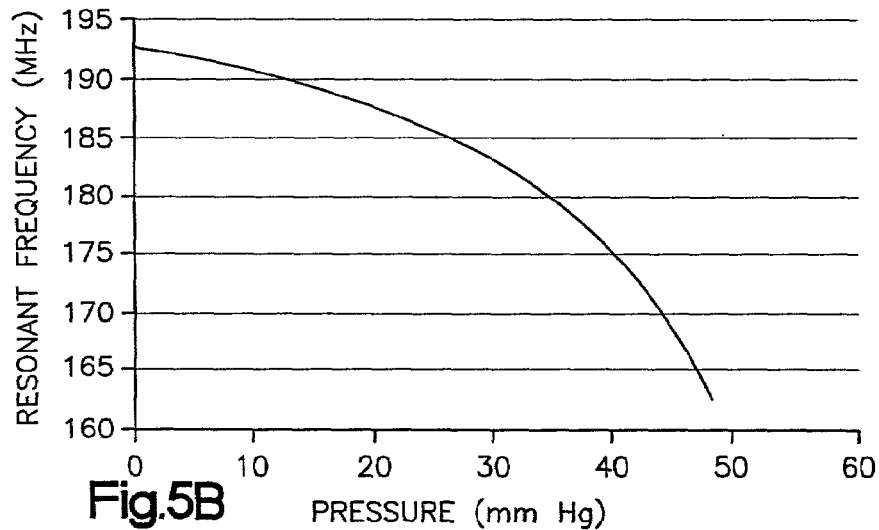
FIG. 5B is a graph illustrating the relationship between resonant frequency of the tonometer sensor and IOP.

As has been described in connection with the illustration of FIG. 3A, the deflection of the diaphragm 20 of the compliant region 18 as the contact surface 14 of the substrate 12 is pressed against the surface portion 34 of the eye 36 is representative of the IOP of the eye. The graph of FIG. 5A illustrates an exemplary center deflection in micrometers ($\mu$m) expected for a diaphragm 20 with the geometry described above as a function of the IOP of the eye expressed in parametric units of millimeters of Mercury (mm Hg). It is this deflection of the diaphragm 20 which causes the change in capacitance and may be measured by the resultant change in resonant frequency of the tank circuit. The graph of FIG. 5B illustrates an estimated change in resonant frequency based upon a conservative approximation of a corresponding change in capacitance resulting from the deflection of the diaphragm 20 due to IOP. The expression of resonant frequency (MHz) to IOP (mm Hg) illustrated by the graph is nonlinear as expected in a capacitive sensing structure for measuring IOP.

Figure 6:
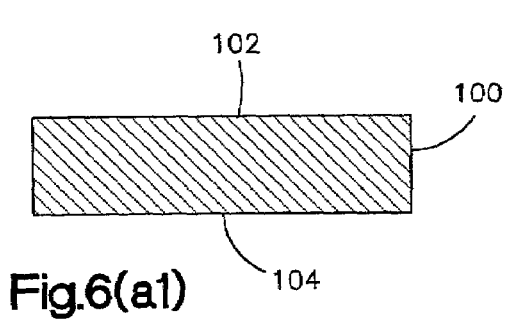
FIGS. 6($a$1)–6($i$2) are cross-sectional and plan views, respectively, of the tonometer sensor through various stages of a fabrication process.
Figure 6:
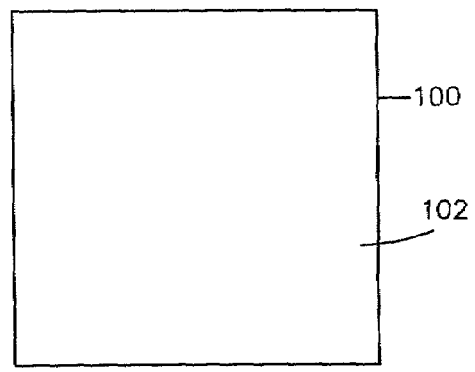
Figure 6:
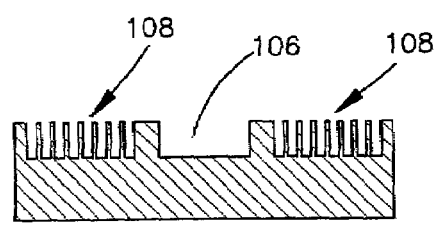
Figure 6:
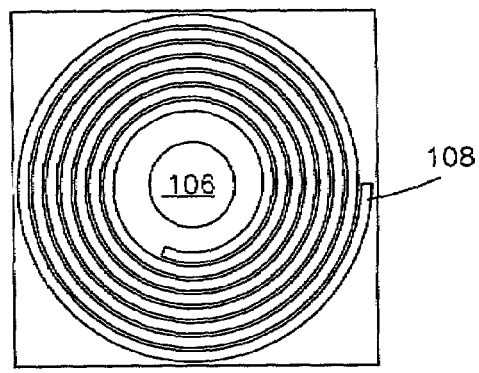
Figure 6:
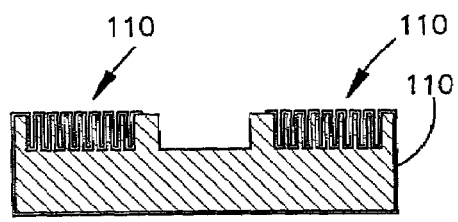
Figure 6:
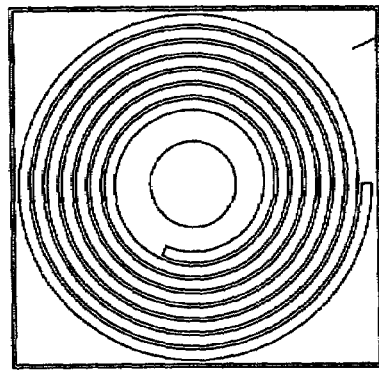
Figure 6:
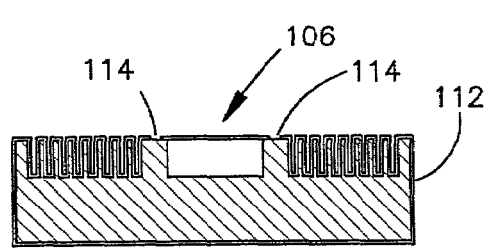
Figure 6:
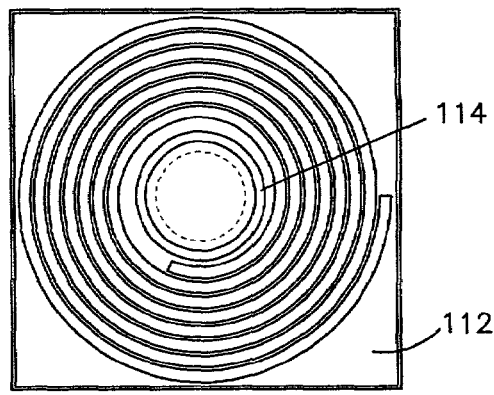
Figure 6:
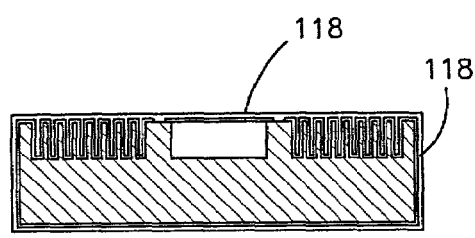
Figure 6:
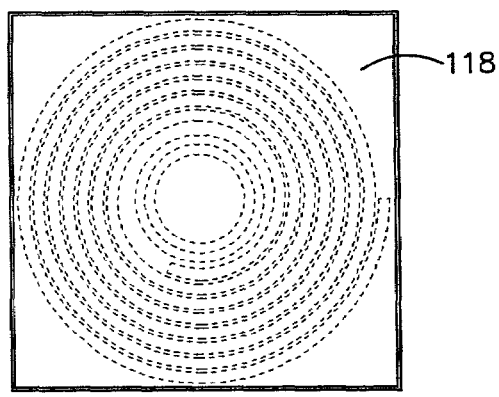
Figure 6:
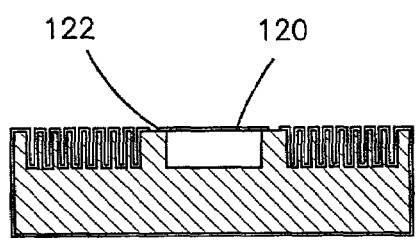
Figure 6:
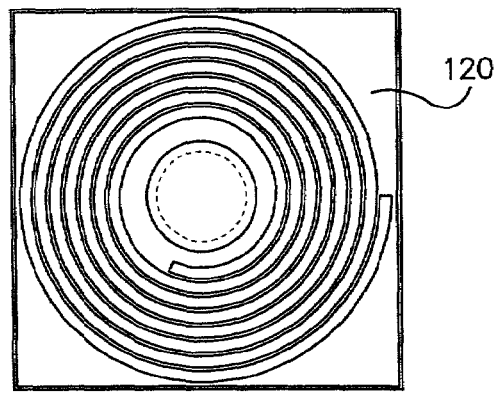
Figure 6:
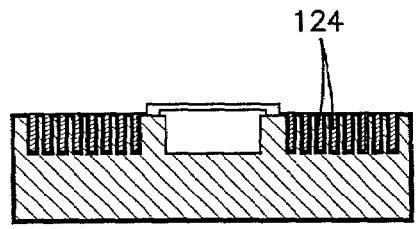
Figure 6:
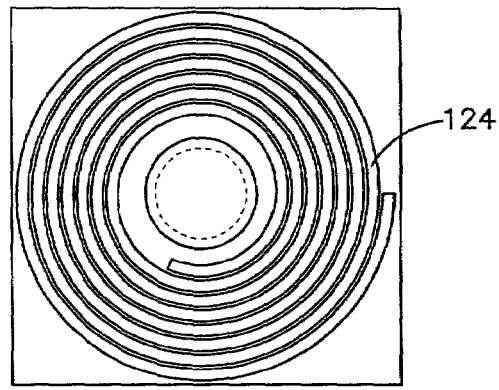
Figure 6:
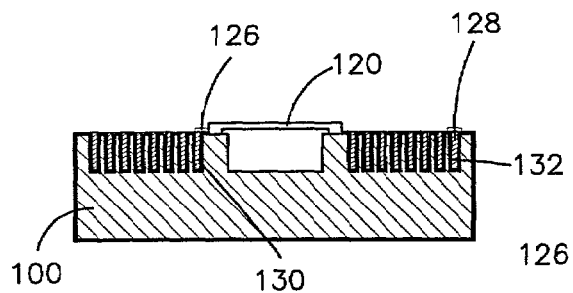
Figure 6:
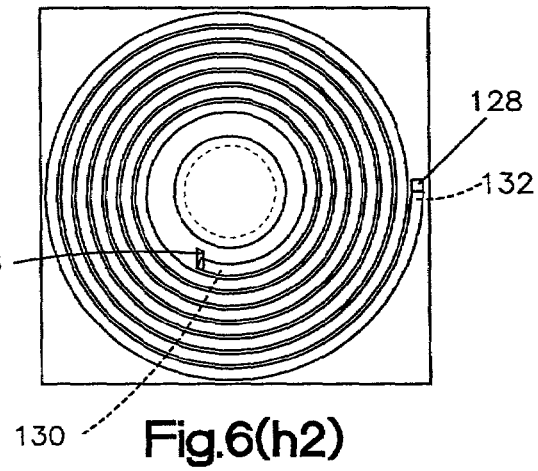
Figure 6:
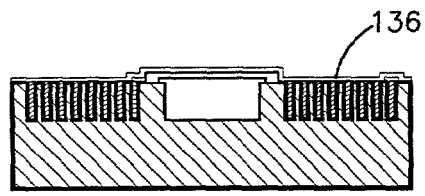
Figure 6:
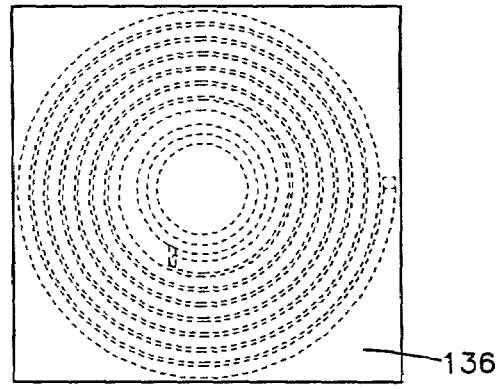

An exemplary process suitable for fabricating an embodiment of the tonometer sensor 10 is shown in the process diagrams of FIGS. 6(a1) through 6(i2) wherein each Figure provides cross-sectional and plan views, respectively, of the sensor structure at various stages of the fabrication process.

The process starts with a substrate 100 which may be part of a silicon wafer, for example, as shown in FIG. 6(a). It is understood that materials other than silicon may be used for the substrate in which case the process may be slightly modified to accommodate such other material. The substrate has a top surface 102 and a bottom surface 104. In the step of FIG. 6(b), an etch resistant layer is provided over the substrate, like silicon dioxide ($SiO_2$), for example, and the top surface 102 is patterned using conventional lithograph/etching processes to form the capacitor well region 106 having a diameter of approximately 500 µm, for example, and spiraled groove regions 108 of a width on the order of 5 µm, for example, for the inductor coil. Thereafter, the unpatterned etch resist areas of the Si substrate are etched using a deep etch process, like reactive ion etching, for example, to a depth of one to twenty microns and the etch resist is removed rendering a structure as shown in FIG. 6(b).

In the step of FIG. 6(c), a layer of silicon nitride ($Si_3N_4$) or other similar material 110 is deposited on the surfaces of the substrate 100. A conformal coating of $Si_3N_4$ is deposited over the surface of the substrate through a conventional chemical vapor deposition (CVD) process to a thickness of approximately 1200 Å–2400 Å, for example. Next, in the step of FIG. 6(d), a layer of low temperature oxide (LTO) 112 is deposited over the $Si_3N_4$ layer 110 by conventional CVD to a thickness of approximately 2–3 µm, for example. The LTO layer 112 of the top surface 102 is polished smooth using a chemical mechanical polishing process, for example, and patterned using a conventional photolithography process to form an anchor region 114 which, for the present embodiment, is in the form of an annulus of a width of approximately 50–100 microns surrounding the capacitive well region 106. The anchor region 114 is etched through the LTO layer 112 down to the $Si_3N_4$ layer 110 using a reactive ion etching process, or a wet etching process using buffered hydrofluoric acid (BHF), or other similar process.

In the step of FIG. 6(e), a layer of polysilicon 118 is deposited, preferably by CVD, over the surface of the LTO layer 112 of FIG. 6(d) and the layer of polysilicon at the top surface 102 is patterned and etched in a conventional manner to form an unetched layer of polysilicon 120 covering substantially the capacitive well region 106 and anchored by region 114 to the nitride layer. A hole 122 may be provided through an edge of the polysilicon layer 120 to the LTO and $Si_3N_4$ layers 112 and 110 thereunder by the aforementioned patterning and etching process of FIG. 6(e). A post annealing process is performed to render the membrane section of polysilicon 120 in tension. In the present embodiment, the structure of FIG. 6(f) is put in an oven and heated for approximately 30 minutes at approximately 900° C. which changes the crystalline makeup of the polysilicon to provide for stress modification thereof.

In the step of FIG. 6(f), the LTO and nitride layers 112 and 110, including the layers under the polysilicon layer 120, are removed, preferably by a conventional BHF etching process wherein the BHF is allowed to flow through the hole 122 and etch the LTO and nitride layers under the polysilicon layer 120 which are released in solution through the same hole 122. Accordingly, a polysilicon diaphragm 120 in tension is produced as shown in FIG. 6(f). Next, the hole 122 in the polysilicon diaphragm is sealed by growing a low temperature oxide layer (not shown) over the hole 122 in a conventional furnace environment.

In the step of FIG. 6(g), the grooved areas 108 may be pretreated to accept a conductive material which may be deposited in the grooves by conventional plating, sputtering or evaporation techniques, for example, to form the inductor coil 124. Metals which may be used for this process include Ni, Au, Fe, Ag, and Pt to name a few. Preferably, the metallic plating is performed electroless, but electroplating may also be used without deviating from the principles of the present invention.

As shown in FIG. 6(h), interconnects 126 and 128 are provided from the ends of the inductor coil 124 to corresponding sides of the capacitive element. For the interconnect region 126, a window is formed in the nitride layer 110 between the conductive material of the inside coil 130 and the polysilicon layer 120 which is one side of the capacitive element of the sensor 10. When the window region is plated, the metal end 130 of the inductor coil 124 will make electrical contact with one side 120 of the capacitive element. For the interconnection region 128, a window is formed in the nitride layer 110 between the substrate and the groove of the other end 132 of the coil 124 such that when plated, metal electrically connects the other end 132 of the coil 124 with the silicon substrate 100, which is the other side of the capacitive element, thus, completing the tank or oscillatory circuit. In the step of FIG. 6(i), a thin layer of non-conducting material 136 may be grown over the metallic plated surfaces of the non-compliant region 16 to ensure against the sections of the inductor coil 124 making contact with each other over the surface of the nitride layer 110.

Figure 7:
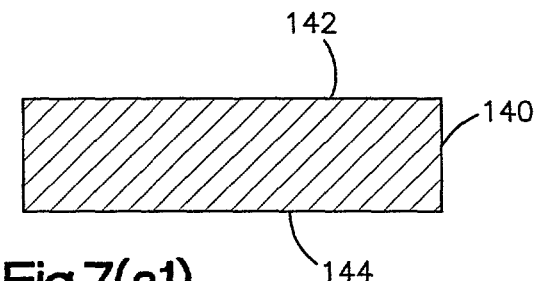
FIGS. 7($a$1)–7($j$2) are cross-sectional and plan views, respectively, of an alternate tonometer sensor through various stages of a fabrication process.
Figure 7:
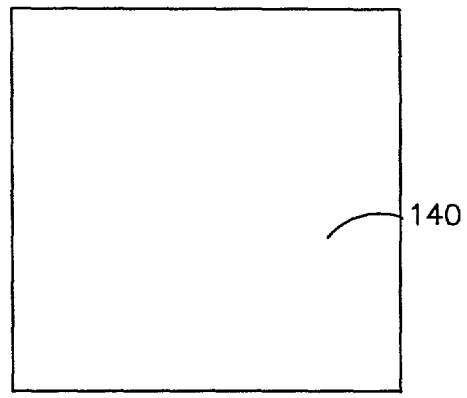
Figure 7:
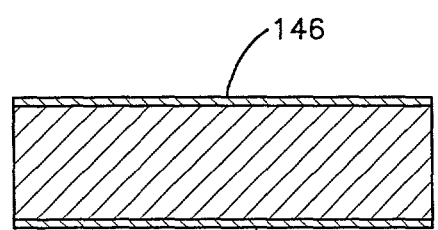
Figure 7:
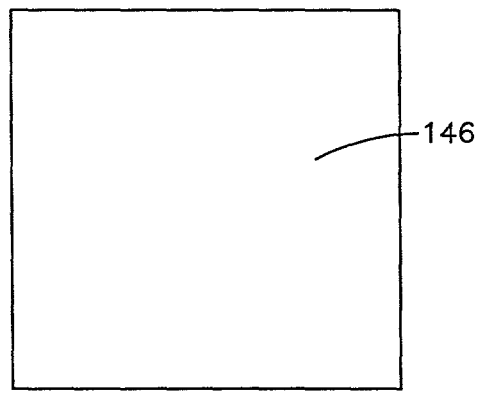
Figure 7:
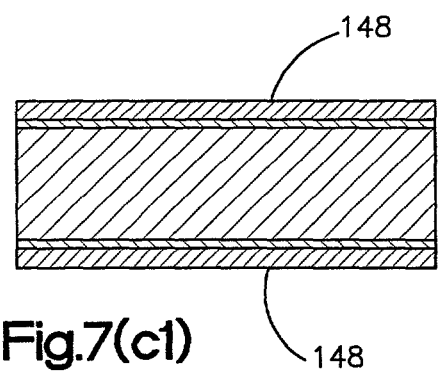
Figure 7:
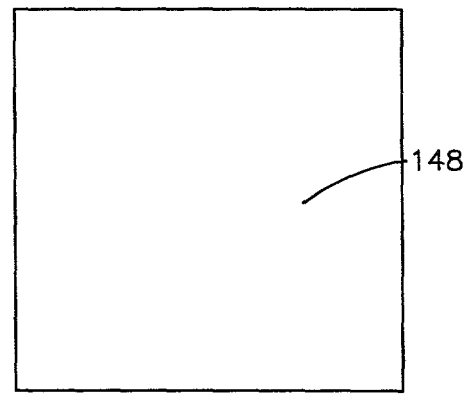
Figure 7:
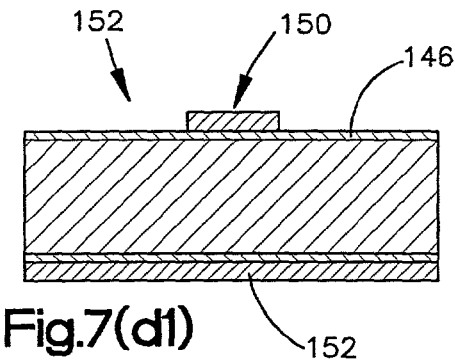
Figure 7:
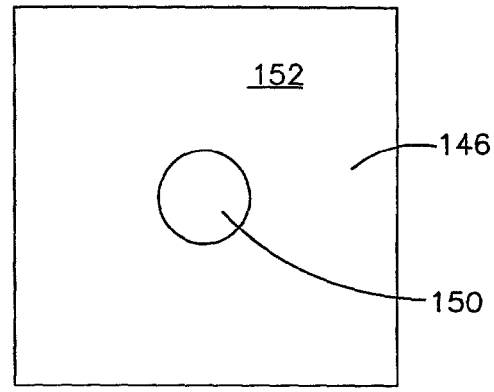
Figure 7:
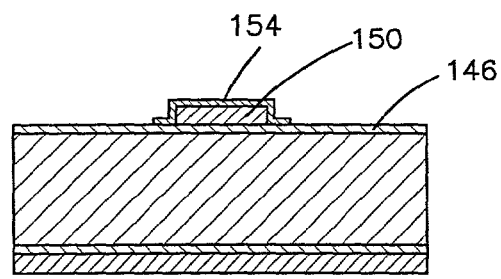
Figure 7:
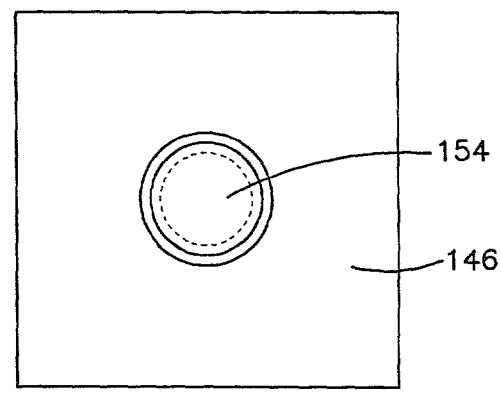
Figure 7:
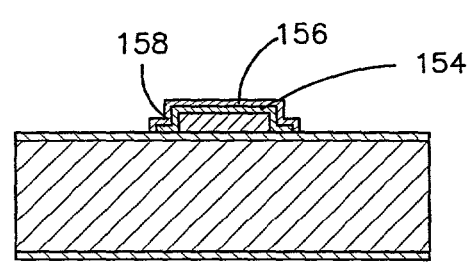
Figure 7:
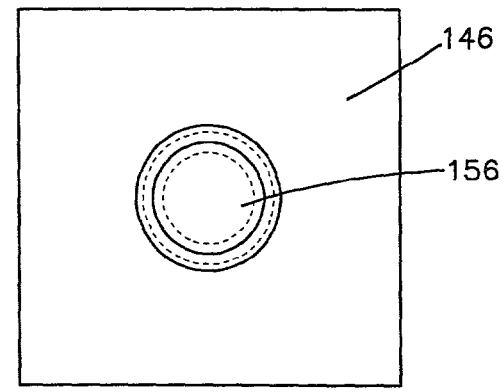
Figure 7:
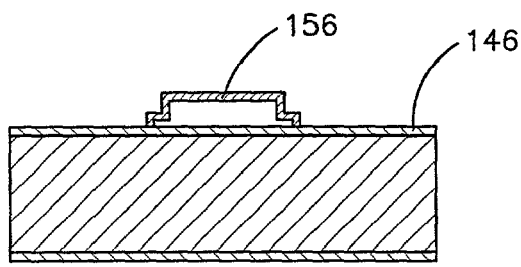
Figure 7:
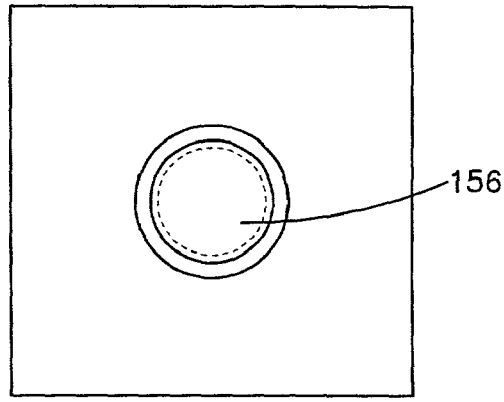
Figure 7:
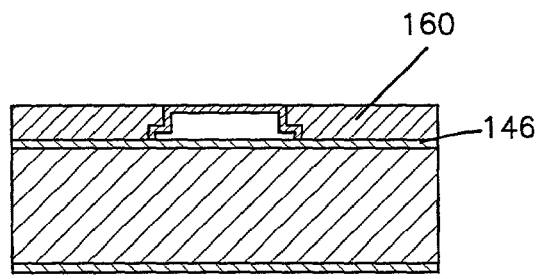
Figure 7:
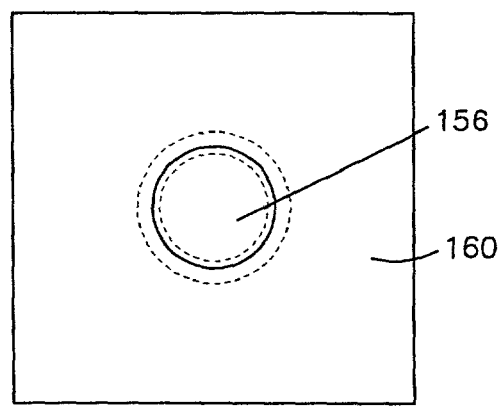
Figure 7:
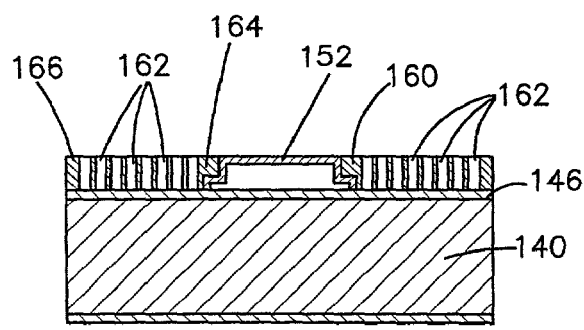
Figure 7:
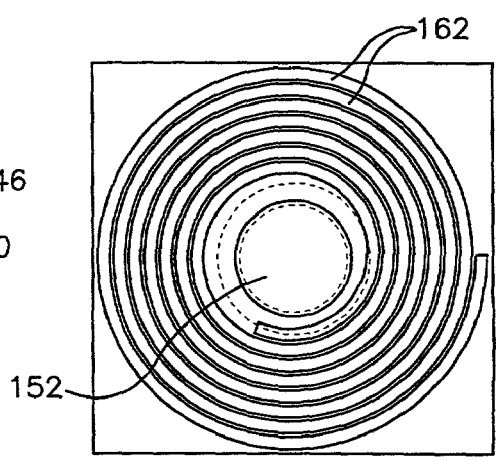
Figure 7:
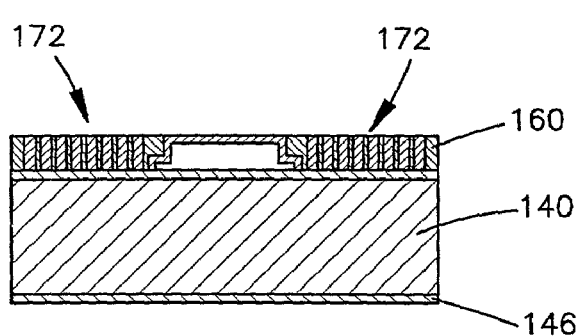
Figure 7:
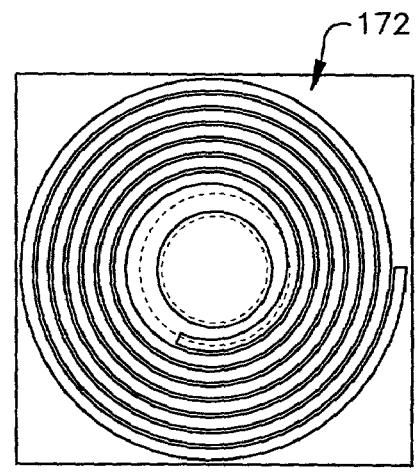

An embodiment for illustrating a fabrication process of an alternate embodiment of the tonometer sensor 10 is shown in the FIGS. 7(a1) through 7(j2) wherein each Figure provides cross-sectional and plan views, respectively, of the alternate sensor structure at various stages of the fabrication process. The process starts with a substrate 140 which may be part of a silicon wafer, for example, as shown in FIG. 7(a). It is understood that materials other than silicon may be used for the substrate in which case the process may be slightly modified to accommodate such other material. The substrate 140 has a top surface 142 and a bottom surface 144. In the step of FIG. 7(b), a layer of silicon nitride ($Si_3N_4$) or other similar material 146 is deposited on the top and bottom surfaces 142 and 144 of the substrate 140. In the present embodiment, the $Si_3N_4$ 146 is deposited through a conventional chemical vapor deposition (CVD) process to a thickness of approximately 1200 Å, for example.

Next, in the step of FIG. 7(c), a layer of low temperature oxide (LTO) 148 is deposited over the $Si_3N_4$ layer 146 by conventional CVD to a thickness of approximately 1.5 µm, for example. The LTO layer 148 of the top surface 142 is patterned using a conventional photolithography process to form a circled region 150 having a diameter of approximately 500 µm, for example, on top of the $Si_3N_4$ layer 146, and the unpatterned regions 152 around the circled region 150 and on the bottom surface 144 are etched using a reactive ion etching process or a wet etching process using buffered hydrofluoric acid (BHF), or other similar process.

The top surface 142 of the resulting structure as shown in FIG. 7(d) is deposited with another low temperature oxide layer, preferably by CVD, to a thickness of approximately 0.5 µm, for example. This second LTO layer 154 is patterned and etched in a conventional manner such that the remaining unetched second LTO layer overlaps the circled layer 150 concentrically to form an annular region of approximately 50 µm on top of the $Si_3N_4$ layer 146 surrounding the circled region 150 as shown in FIG. 7(e).

In the step of FIG. 7(f), a layer of polysilicon is deposited, preferably by CVD, over the top surface 142 of the structure of FIG. 7(e), and the layer of polysilicon is patterned and etched in a conventional manner to form an unetched layer of polysilicon 156 covering substantially the second LTO layer 154. A hole 158 may be provided through the polysilicon layer 156 to the LTO layers 150, 154 thereunder by the aforementioned patterning and etching process of FIG. 7(f). A post annealing process is performed to render the membrane section of polysilicon 156 in tension. In the present embodiment, the structure of FIG. 7(f) is put in an oven and heated for approximately 30 minutes at approximately 900° C. which changes the crystalline makeup of the polysilicon to provide for stress modification thereof.

In the step of FIG. 7(g), the LTO layers 150 and 154 under the polysilicon layer 156 are removed by a conventional BHF etching process wherein the BHF is allowed to flow through the hole 158 and etch the LTO layers under the polysilicon layer 156 which are released in solution through the same hole 158. Accordingly, a polysilicon diaphragm 156 in tension is produced. Next, the hole 158 in the polysilicon diaphragm is sealed by growing a low temperature oxide layer over the hole in a conventional furnace environment.

Next, in the step of FIG. 7(h), a polymer layer 160 which may be a photosensitive polyimide, a photoresist material, PMMA, or the like, is deposited over the $Si_3N_4$ layer 146 of the top surface 142. Patterning of the polymer layer depends on the type of polymer used. For example, if a polyimide is used, conventional photolithography may be used to form the annular winding pattern of the inductor coil 124. The patterned portions of the polyimide are etched conventionally down to the $Si_3N_4$ layer 146 to provide grooves 162 in which to plate the metallic material of the inductor coil 124 within the polyimide layer 160 on the $Si_3N_4$ layer 146 as shown in FIG. 7(i). Preferably, the metallic plating is performed electroless, but electroplating may also be used without deviating from the principles of the present invention. One groove 164 in the polyimide layer 160 goes down to the annulus of the polysilicon layer 156 so that when plated, the metal end of the inductor coil 124 will make contact with the polysilicon 156 which is one side of the capacitive element of the sensor 10. In addition, a hole may be provided through the $Si_3N_4$ layer 146 at the groove 166 of the other end of the inductor coil 124 to allow the plated metal in the groove 166 to pass through the hole and make contact with the silicon substrate 140, which is the other side of the capacitive element, thus completing the tank or oscillatory circuit. As shown in FIG. 7(j), a thin layer of non-conducting material may be grown over the metallic plated surfaces 172 of a non-compliant region to ensure against the sections of coil making contact with each other over the surface of the polyimide layer 160.

While the present MEMS sensor 51 is described as being fabricated on a silicon substrate, it is understood that other substrates may be used such as a polymeric material, including plastics and polymer films, for example. Such an alternate MEMS sensor 51 could be fabricated using a well-known micro-replication process such as is illustrated in FIGS. 8(a)–8(d), with the simultaneous fabrication of two of the sensors 51 being shown side by side. In FIGS. 8(a1) and 8(a2), a thin film of plastic or polymer is mechanically patterned, preferably with dimples that would represent wells 54, by a conventional process. The film 52 would then be metalized to form a ground electrode 56. A second film 58 (FIG. 8(b1)) could be metalized in a pattern to form an inductor 60 and capacitor (tank circuit). The two films 52 and 58 are then aligned and ultrasonically bonded together. Following a final metallization step (FIG. 8(d)) in which a metal is passed through a hole 59 in the second film 58 to form interconnecting conductors 61, the tonometer sensor 51 has a structure similar to the structures described herein above for a silicon substrate, but made from a plastic or polymer film instead.

Figure 9:
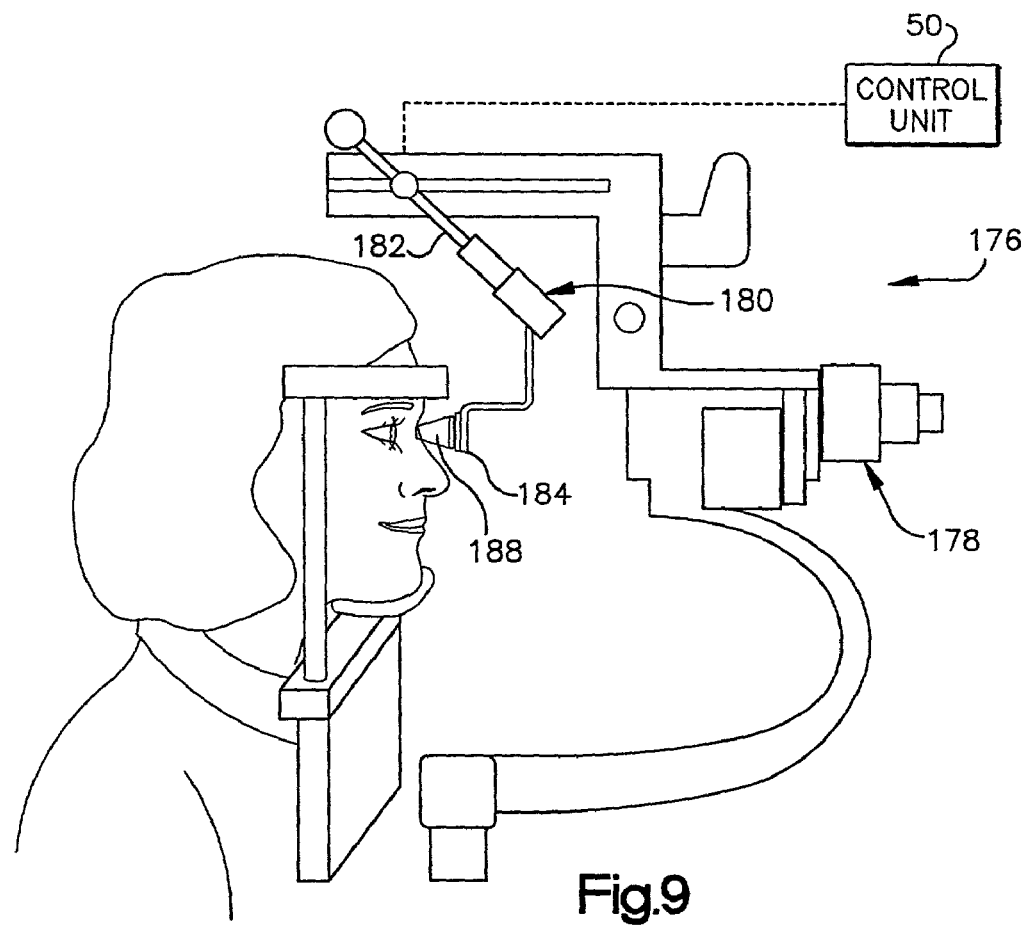
FIG. 9 is an illustration of an apparatus for measuring IOP of an eye using the tonometer sensor of FIG. 3.

Referring now to FIG. 9, an apparatus 176 that uses the sensor 10 to measure IOP is illustrated. The apparatus 176 comprises a known slit lamp biomicroscope 178 with an applanation tonometer mechanism 180. On the slit lamp biomicroscope 178, the applanation tonometer mechanism 180 includes one or more movable arms 182 that are adjustable by dials (not shown) and/or levers (not shown), as is known in the art, to move the sensor 10 which is mounted, as described below, at the distal end of the mechanism into contact with an eye for IOP measurement. It should be understood that one or more stepper motors could also be used in the applanation tonometer mechanism 180 to adjust and advance the position of the applanation tonometer mechanism.

Figure 10A:
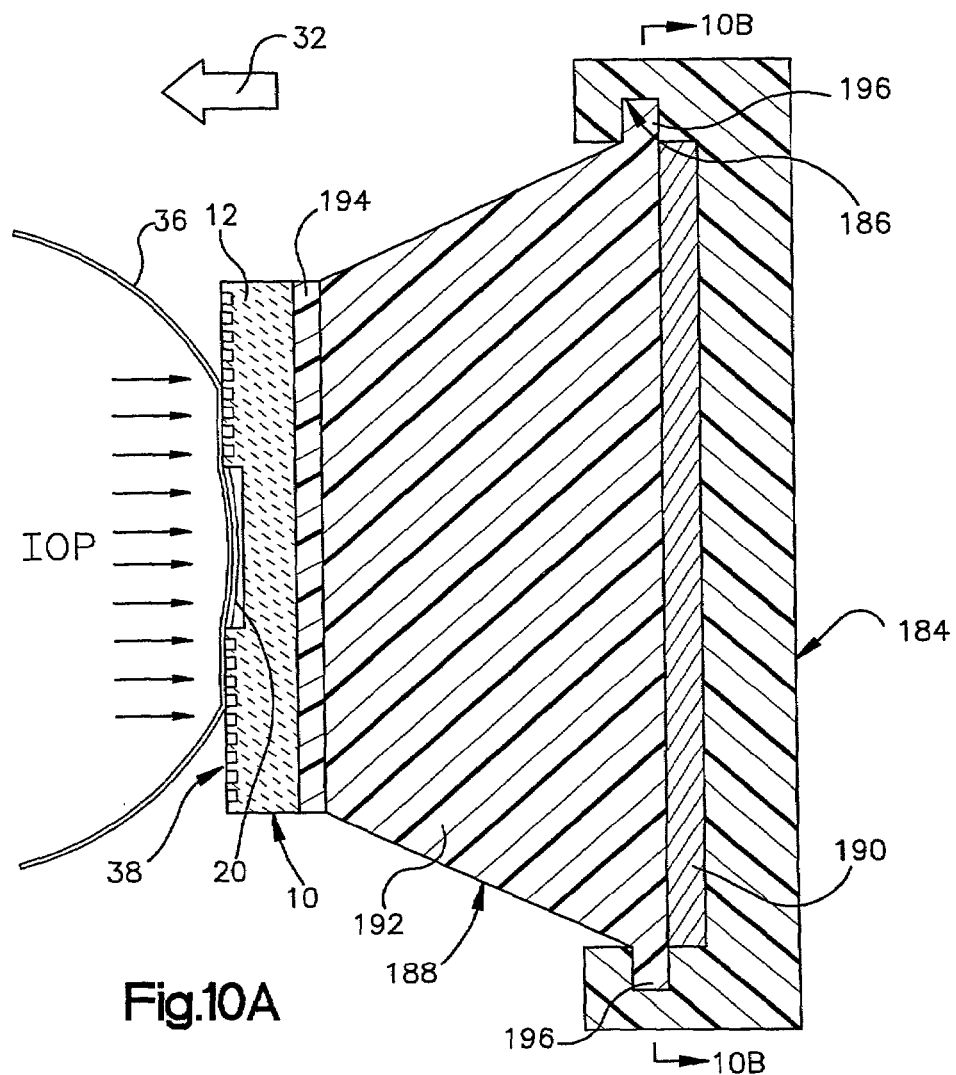
FIG. 10A is an illustration of the tonometer sensor mounted in a disposable carrier and attached to an end of the apparatus of FIG. 9.
Figure 10B:
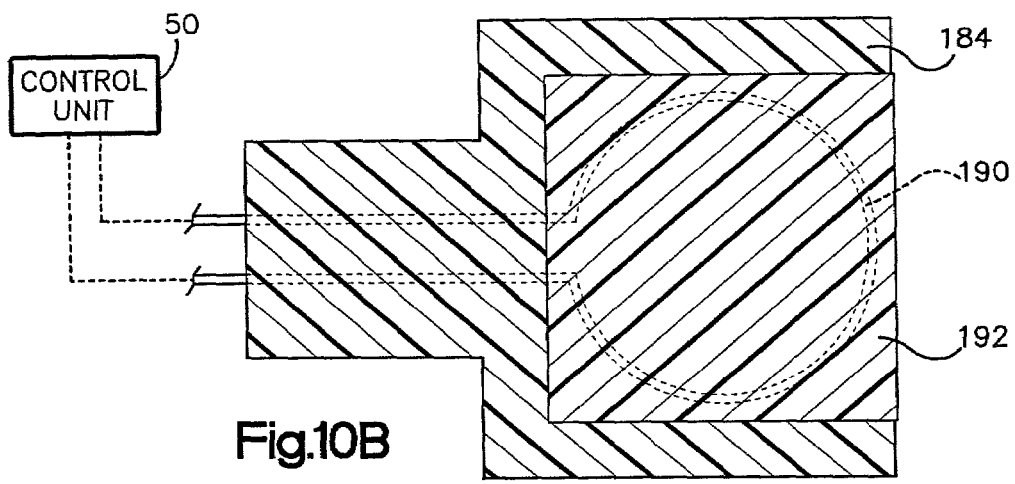
FIG. 10B is a sectional view taken along line 10B—10B in FIG. 10A.

At its distal end, the applanation tonometer mechanism 180 includes a holder 184 (FIGS. 10A and 10B) to which the sensor 10 is attached. The holder 184 includes a slot 186 for receiving a sensor module 188 and an antenna 190 (shown schematically in FIG. 10A) for transmitting to and receiving electrical signals from the tank circuit on the sensor 10. The sensor module 188 comprises the sensor 10 which is attached to a dielectric sensor carrier 192 by a dielectric adhesive 194, such as an epoxy. The sensor carrier 192 includes a pair of oppositely disposed flanges 196 that snap-fit into the slot 186 in the holder 184, although it should understood that the attachment between the sensor carrier 192 and the holder 184 could have many different configurations.

As the contact surface of the tonometer sensor 10 is pressed against the surface portion of the eye, the response of the tonometer sensor 10 over time is shown in the illustrations of FIGS. 11A1 through 11E2. Each of the FIGS. 11A through 11E provide an illustration of the position of the sensor 10 in relation to the eye 36 and a corresponding time graph of a pressure representative signal vs. time. The darkened region along each time graph is the time interval represented by the respective illustration. In FIG. 11A, advancing the sensor 10 toward the cornea surface of the eye 36 causes the sensor to flex. In FIG. 11B, the compliant region 18 of the sensor 10 initially meets the surface of the eye 36. The initial dip in pressure at 60 from the base line pressure 62 may be due to surface tension attracting the diaphragm of the compliant region 18 just before actual contact with the eye surface.

Accordingly, as the sensor 10 is pressed further against the eye surface and the diaphragm is depressed as shown in FIG. 11C, the pressure representative signal will continue to increase. As the flattening of the eye surface increases, the sensed pressure peaks, as shown at point 64 in FIG. 11D, starts to decrease as a result of the bending forces of the cornea being transferred from the compliant region 18 to across the non-compliant region 16 of the sensor 10. Point 64 represents the initial crest of the pressure representative signal. As the sensor 10 is pressed further against the eye surface as shown in FIG. 11E, the pressure reaches a minimum at point 66 and this minimum represents the IOP of the eye 36. Thereafter, as the sensor 10 is moved farther toward and against the eye surface, the pressure increases beyond the IOP stage due primarily to an artificial elevation of IOP resulting from additional applanation and other forces in the eye, such as, surface tension from tearing shown at 68, bending force shown at 70, and tissue tension shown at 72, for example. After the IOP has been measured via the sensor 10, the sensor is returned back to its original starting position and the pressure reading is baselined at level 62. The sensor 10 is then ready for the next IOP measurement.

In order to take the IOP measurements from the sensor 10, a control unit 50 (FIGS. 9 and 10B) is provided and is operatively coupled, in a manner not shown, to the antenna 190 in the holder 184. The control unit 50 generates the activation signal for energizing the impedance element of the sensor 10 to measure a signal representative of the IOP. This activation signal is preferably an electromagnetic signal that varies over a predetermined radio frequency range say from one hundred to two hundred megahertz (100–200 MHz), for example, that energizes the tank circuit of the sensor 10 and causes it to resonate. The control unit 50 may also include a circuit to detect the resonant frequency of the sensor's tank circuit which is proportional to the IOP as shown by the graph of FIG. 5B, for example. This activation signal may be transmitted from the control unit 50 multiple times over a predetermined time interval during which the sensor 10 is in contact with the eye 36. Each electromagnetic activation signal is ramped from a starting frequency $f_1$ to an ending frequency $f_2$ in order for a resonant frequency to be determined which is representative of a pressure measurement sampling point during the application of the sensor 10 to the eye 36. The collection of this pressure measurement data (or sampling points) provides for a pressure vs. time graph, as exemplified by FIG. 11E, in order to determine the minimum or actual IOP.

Figure 12:
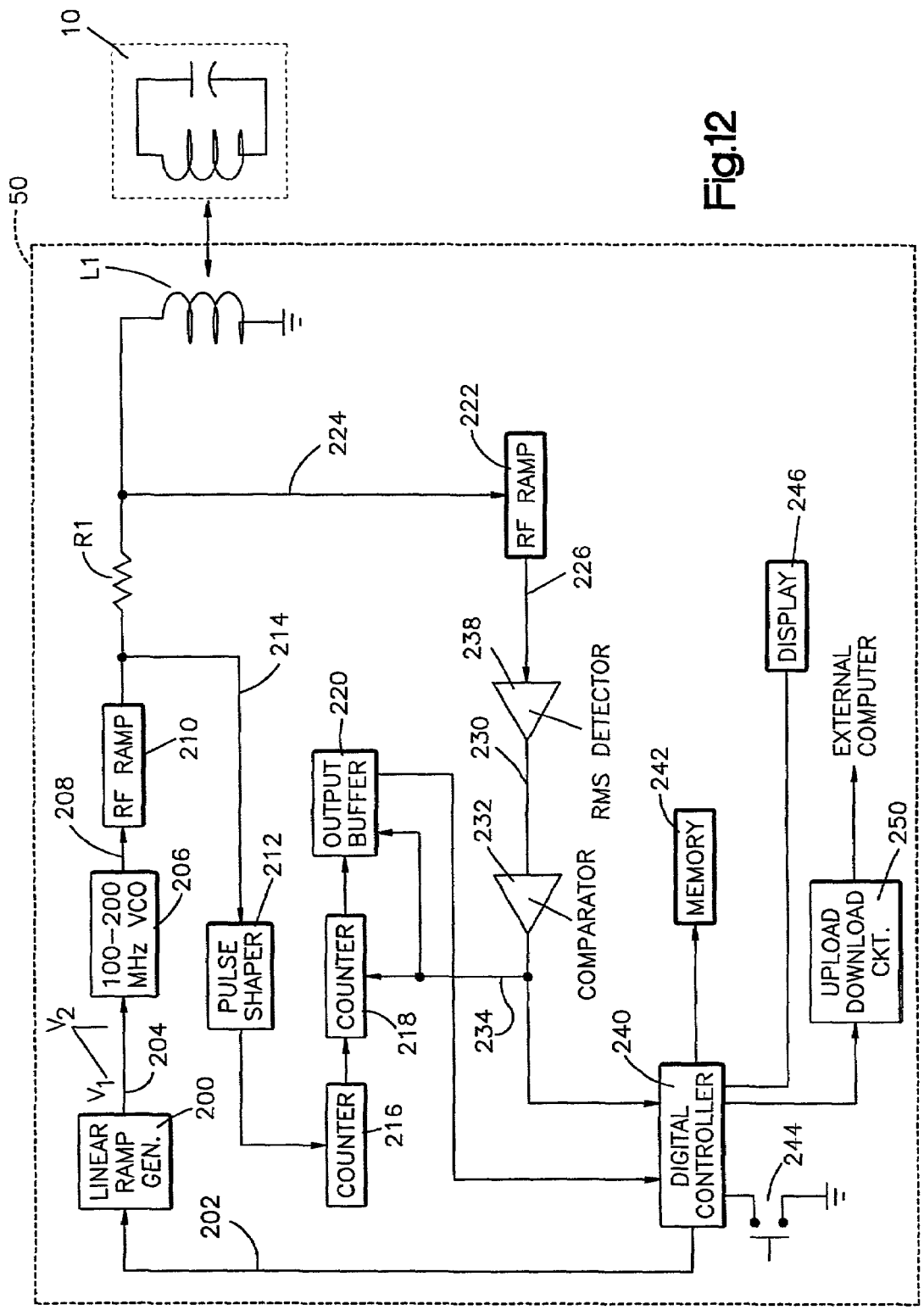
FIG. 12 is a functional block diagram schematic of a control unit for use with the apparatus of FIG. 9.

A schematic block diagram of the control unit 50 for use in of the present invention is shown in FIG. 12. Referring to FIG. 12, a circuit 200 may be triggered by a signal 202 to generate a linear ramping signal 204 which ranges from voltages V1 to V2 over a predetermined time interval $\Delta t$, on the order of 1 millisecond, for example. At the end of the time interval $\Delta t$, the voltage returns to a predetermined voltage setting to wait for the next trigger signal over line 202. The linear ramping signal 204 governs a voltage controlled oscillator (VCO) circuit 206 to generate a sinusoidal signal 208 which overlaps the frequency range of the sensor 10 as the signal 204 ramps from V1 to V2. The signal 208 may be amplified by a radio frequency (RF) amplifier circuit 210 which drives a resistor/inductor series combination, R1 and L1, respectively. The output of the RF amplifier 210 may be provided to a pulse shaper circuit 212 over signal line 214 which in turn is coupled to a cascaded pair of digital counters 216 and 218. The digital output of counter 218 is captured in an output buffer 220.

The voltage across the inductor L1 is input to another RF amplifier 222 via signal line 224. The output 226 of the RF amplifier 222 is provided to a root-mean-square (RMS) detector 228, the output 230 of which being coupled to a comparator circuit 232. In the present embodiment, the comparator circuit 232 functions as a signal peak or valley detector and generates a signal over line 234 when the signal peak or valley is detected. The signal line 234 is coupled to the counter 218 and output buffer 220 for operation thereof. The circuits of the control unit 50 may be centrally controlled in operation by a digital controller 240, which may be a programmed microprocessor, digital signal processor or a combination of hardwired digital logic circuits. A memory unit 242 is coupled to the digital controller 240 and may be comprised of a combination of static, dynamic and read-only memory units, for example, for the storage of data and program information. A switch 244 which may be of the push button variety, for example, is coupled to the digital controller 240 through conventional input-output circuitry (not shown). The digital controller 240 may also be coupled to a conventional display unit 246 for displaying IOP readings. The control unit 50 may also include an upload/download circuit 250 for transmitting data between the digital controller 240 and an external computer, like a PC, for example, over a hardwired connection.

Taking an IOP reading using the control unit 50 in combination with the sensor 10 will now be described in connection with FIGS. 9, 10A, 10B, 11E, and 12. A coarse alignment of the sensor 10 with the eye 36, as illustrated in FIG. 9, is done by the doctor or technician looking through the slit lamp biomicroscope 176. The dials/levers of the applanation tonometer mechanism 180 are then adjusted by the operator until the sensor 10 is moved to the position of FIG. 11A1. Once the sensor 10 is brought in close proximity to the eye 36 as shown in FIG. 11A1, the switch 244 may be depressed for taking an IOP reading. In response to the depression of the switch 244, the digital controller 240 commences with a sequence-of control operations to perform the IOP reading.

Following pushing of the switch 244, trigger signals are generated at predetermined times over signal line 202 to cause the linear ramp circuit 200 to generate the ramping signals which controls the VCO circuit 206 to drive the inductor L1 via RF amplifier circuit 210 and resistor R1. In turn, the inductor L1 is coupled magnetically to the inductor of the sensor 10 and electromagnetically activates and drives the tank circuit of the sensor. As has been described herein above, the capacitive element (compliant region 18) of the sensor 10 will change in impedance as it is forced against the surface portion 34 of the eye 36. This change in impedance will cause a change in circuit resonance. Sensor readings are thus taken at the points of resonance of the magnetically coupled circuits. More specifically, during the time interval of each frequency ramp, the RMS voltage across the inductor L1 is monitored by the circuits 222, 228, and 232 to establish the point in time of resonance. At resonance, a signal is generated by the comparator circuit 232 to the digital controller 240, the counter 218, and the output buffer 220. In response to this signal, the digital count of the counter 218 which is representative of the resonance frequency is captured in the output buffer 220 and subsequently, read by the controller 240 and stored in the memory 242. When the digital count has been read and stored, the control unit 50 generates an audible signal to indicate to the operator that it is time to move the sensor 10 to the subsequent position as shown in FIGS. 11A–11E. The stored digital counts of each of the frequency sweep time intervals represent sampled data points which together form the pressure profile of FIG. 11E. The digital controller 240 processes these sampled data points to determine the current IOP reading which may be day and time stamped and stored in the memory 242 and displayed in the digital display 246.

Figure 13:
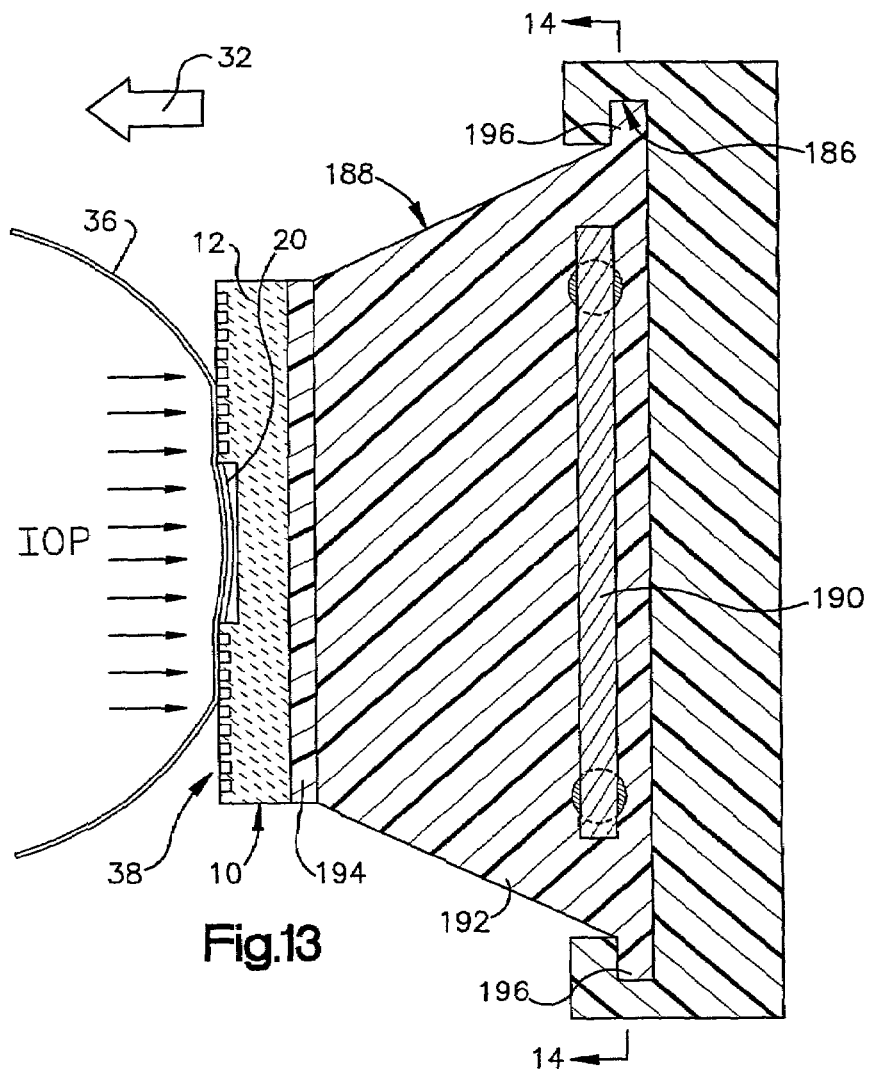
FIG. 13 is an illustration of the tonometer sensor mounted in a carrier constructed in accordance with an alternate construction of the first embodiment.
Figure 14:
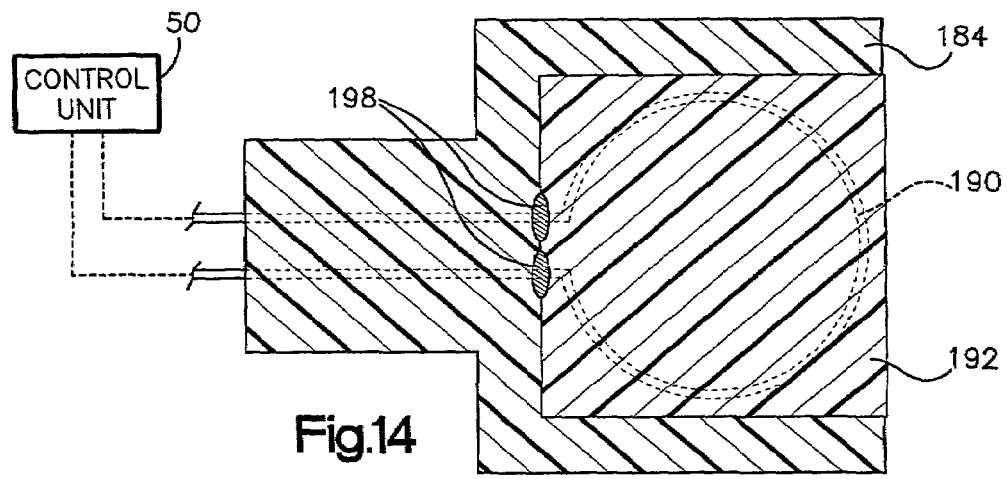
FIG. 14 is a sectional view taken along line 14—14 in FIG. 13.

FIGS. 13 and 14 illustrate an alternate construction for the first embodiment of the present invention in which the antenna 190 is integrated into the disposable sensor carrier 192. When the sensor carrier 192 is inserted into the slot 186 in the holder 184, electrical connection between the antenna 190 and the control unit 50 is made by contacts 198 at one end of the carrier engaging contacts on the holder. In all other aspects, the structure and function of the alternate construction illustrated in FIGS. 13 and 14 is the same as previously described.

FIGS. 15–20 illustrate a tonometer sensor 10' constructed in accordance with a second embodiment of the present invention. In FIGS. 15–20, reference numbers that are the same as those used in FIGS. 1–14 designate components and features that are the same.

Figure 15:
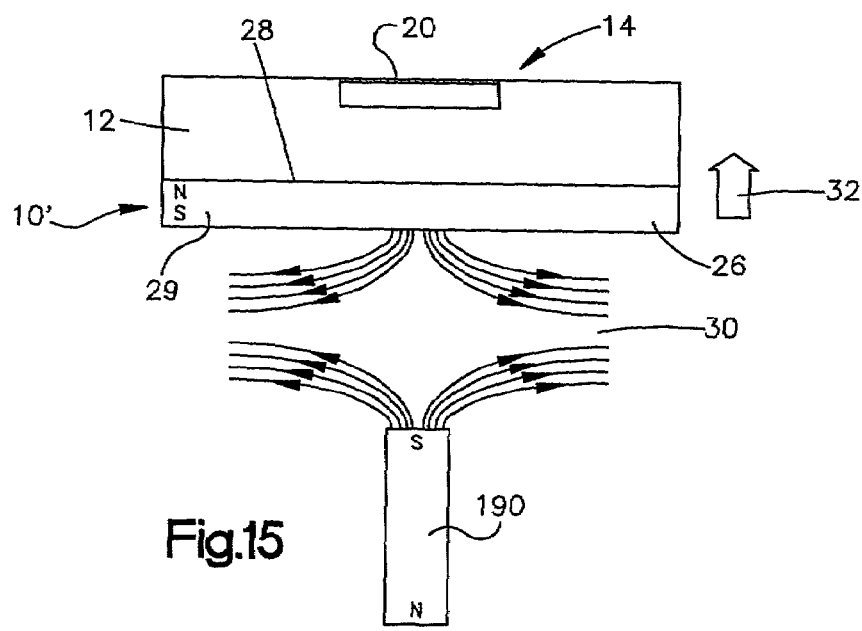
FIG. 15 is a sectional view of a tonometer sensor constructed in accordance with a second embodiment of the present invention, the sensor being shown responding to a magnetic field.

As may be seen in FIG. 15, the substrate 12 of the tonometer sensor 10' includes a region of material 26 that is responsive to a non-invasive external force to press the contact surface 14 against the surface portion 34 of the eye 36 and thereby cause the compliant region 18 (diaphragm 20) to change shape in proportion to the IOP of the eye (refer again to FIG. 3A). The region of material 26 comprises a magnet responsive to a magnetic field 30 as shown in FIG. 15. The surface 28 of the substrate 12 is layered with a magnetic material that forms a permanent magnet 29 with its North-South poles aligned along an axis transverse to the contact surface 14. The magnetic material may be plated or bonded to the surface 28 and may include plated Permalloy, plated iron, plated CoNiMnP, a screen printed polymer composite, and rolled magnetic films. In use, as a magnetic field is brought in proximity to the permanent magnet 29, the substrate 12 is repulsed by the magnetic field with a force 32. The strength of the magnetic field determines the force 32 at which the contact surface 14 is pressed against the surface portion 34 of the eye 36. It should be understood that the magnet 29 could also be plated to the sensor 51 of FIGS. 8(a1)–8(d) so that the micro-replicated sensor 51 could be substituted in the embodiment of FIGS. 15–20.

Figure 17:
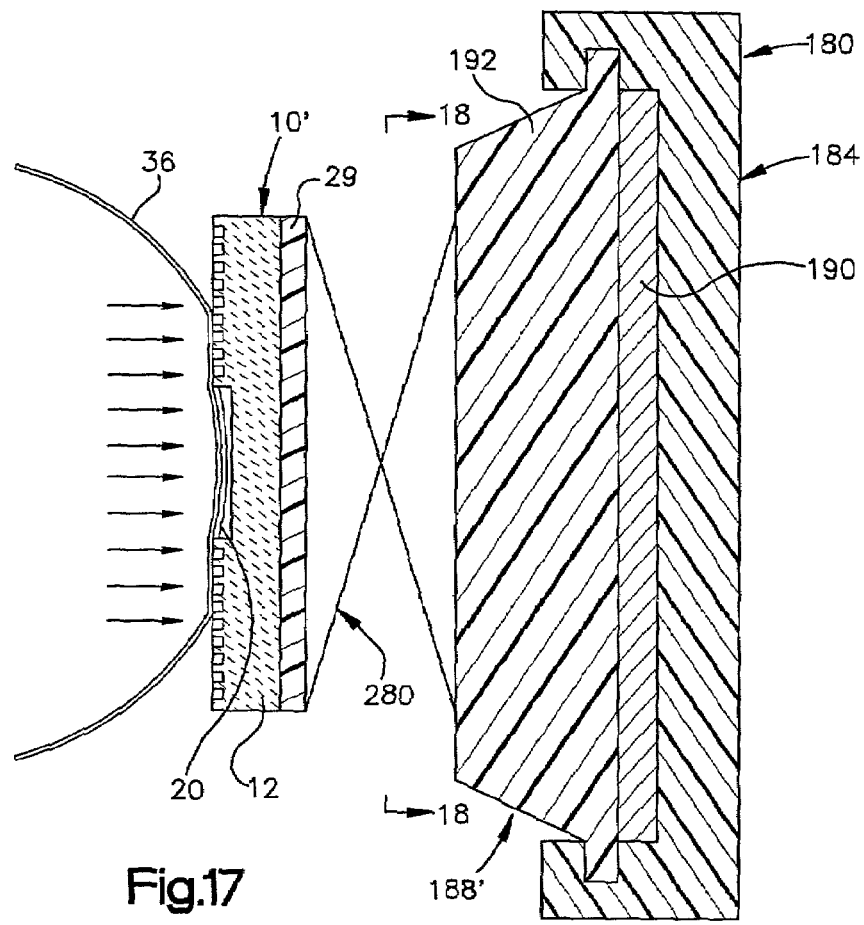
FIG. 17 is a schematic illustration of the tonometer sensor mounted in a carrier constructed in accordance with the sensor embodiment.
Figure 18:
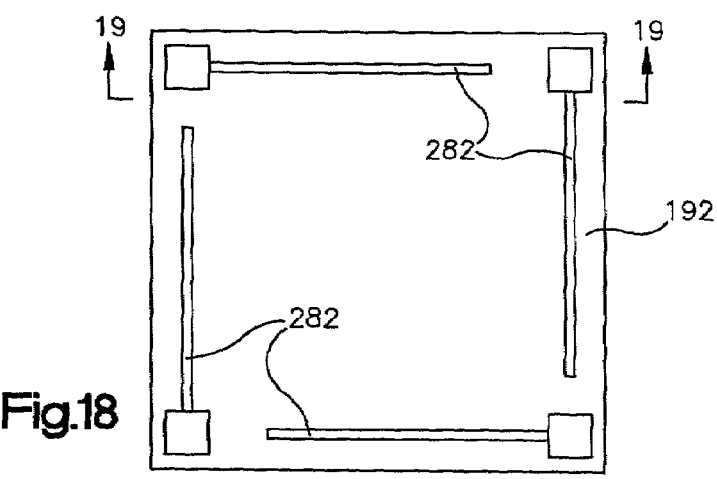
FIG. 18 is a sectional view taken along line 18—18 in FIG. 17.
Figure 19:
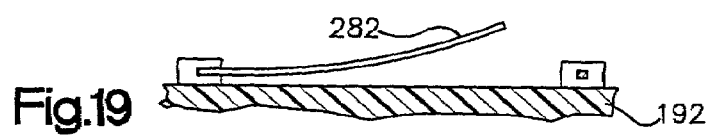
FIG. 19 is a sectional view illustrating a configuration for a portion of FIG. 17.
Figure 20:
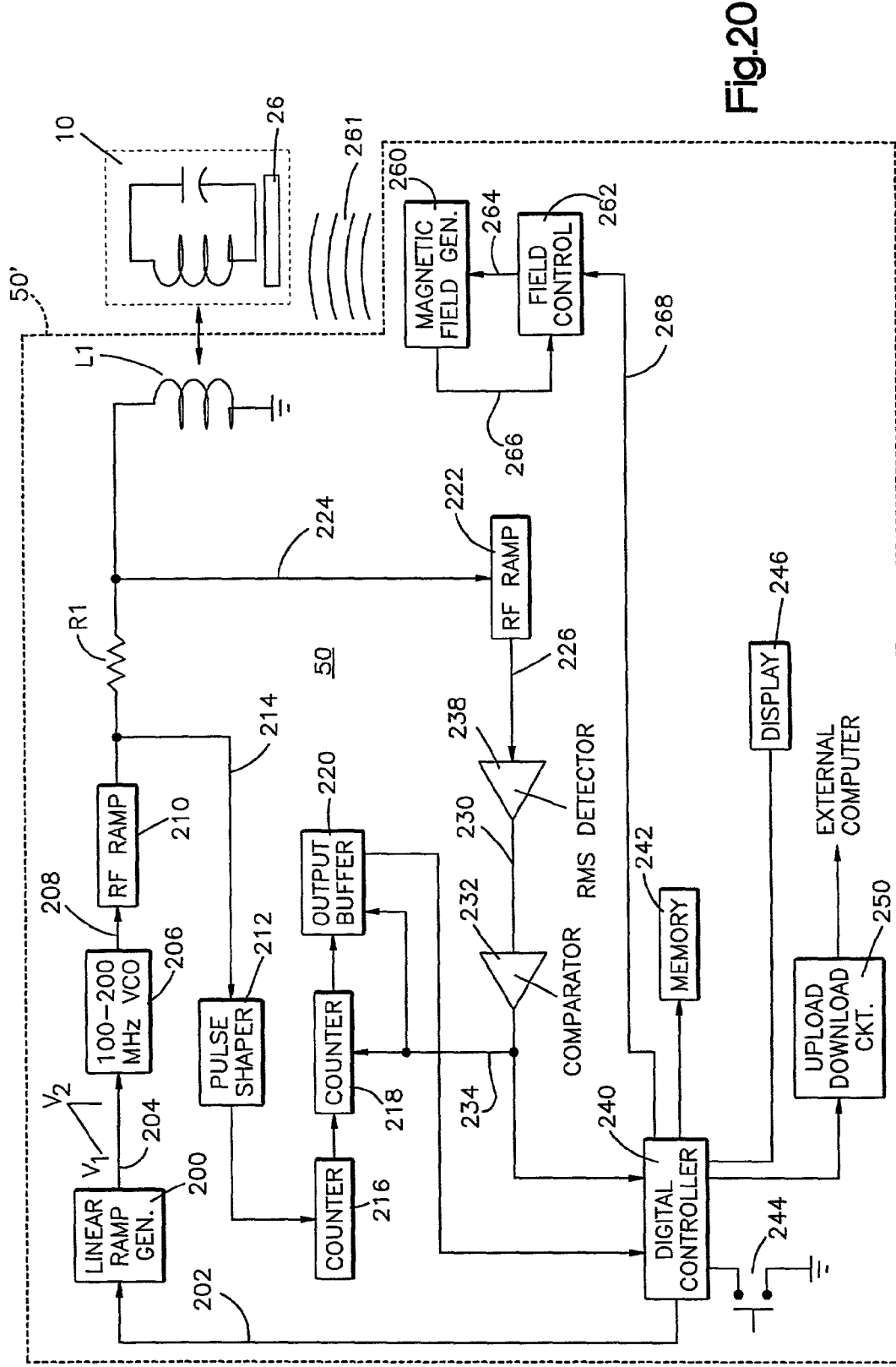
FIG. 20 is a functional block diagram schematic of a control unit for use with the apparatus of FIG. 17.

Referring now to FIG. 17, a sensor module 188', which includes the tonometer sensor 10', is used with the slit lamp biomicroscope 178 (FIG. 9) and the applanation tonometer mechanism 180 to measure IOP. The tonometer sensor 10' of FIG. 17 is connected to the sensor carrier 192 by spring means 280. In one embodiment illustrated in FIGS. 18 and 19, the spring means 280 comprises a plurality of spring arms 282 that are attached, by epoxy or other suitable means, to both the tonometer sensor 10' and the carrier 192. The spring arms 282 allow relative axial movement of the tonometer sensor 10' in response to an electromagnetic activation signal as discussed further below.

Figure 16A:
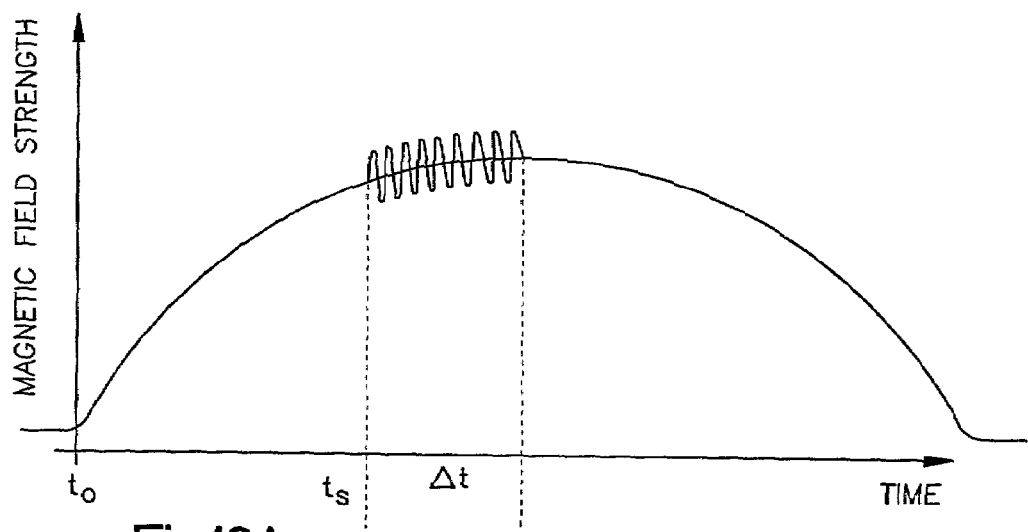
FIG. 16A is a time graph illustrating a magnetic field strength vs. time envelope for the tonometer sensor of FIG. 15.

In order to activate the magnet 29, a control unit 50' (FIG. 20) includes a magnetic field generation unit 260 which is a conventional coil circuit for generating a magnetic field 261 electromagnetically. The magnetic field generation unit 260 may be constructed integrally with the antenna 190 and located at the distal end of the applanation tonometer mechanism 180. A magnetic field control circuit 262 is included to control the magnetic field strength according to the time curve shown in FIG. 16A by adjusting a current signal 264 applied to the field generation unit 260. A feedback signal 266 may be supplied from the field generation unit 260 to the control unit 262 to provide for a more accurate magnetic field strength vs. time profile generation. An initiation signal is provided from the digital controller 240 to the field control unit 262 over a signal line 268. Alternatively, the activation signal from the RF amplifier 210 may be capacitively coupled to the field control circuit 262 for superimposing the activation signal on the magnetic field signal as shown in the profile of FIG. 16A. A further alternative would be to control the magnetic field strength through the RF amplifier by varying the DC bias thereto in accordance with the profile of FIG. 16A.

In use, following rough alignment of the applanation tonometer mechanism 180, with the sensor module 188' attached thereto, to the eye 36, the control unit 50' generates the magnetic field 30 over a predetermined time interval to create the repulsive force 32 that presses the contact surface 14 against the eye 36. The strength of the magnetic field 30 may be varied by the control unit 50' over the predetermined time interval to cause the contact surface of the sensor 10' to be pressed against, and subsequently released from, the surface portion of the eye with a respective varying force.

The graph of FIG. 16A illustrates the magnetic field strength envelope over a time interval of one to two seconds.

Figure 16B:
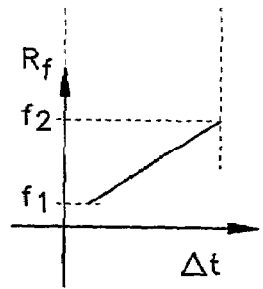
FIG. 16B is a graph illustrating the frequency sweep of an activation signal over a time interval for the tonometer sensor of FIG. 15.

The electromagnetic activation signal may be superimposed on the magnetic field signal illustrated in FIG. 16A. For each interval $\Delta t$ which is much smaller than the predetermined time interval over which the magnetic field is being applied, the electromagnetic signal is ramped from a starting frequency $f_1$ to an ending frequency $f_2$ as illustrated in FIG. 16B. The range of all possible frequencies representative of measured IOP's during the application of the magnetic field will fall within the frequency range of FIG. 16B. Accordingly, for each interval $\Delta t$, a resonant frequency is determined which is representative of a pressure measurement sampling point during the application of the magnetic field and the collection of these pressure measurement sampling points provides for a pressure vs. time graph, as exemplified in FIG. 11E, in order to determine the minimum or actual IOP.

From the above description of the invention, those skilled in the art will perceive improvements, changes and modifications. Such improvements, changes and modifications within the skill of the art are intended to be covered by the appended claims.

We claim:

1. An apparatus for measuring intraocular pressure of an eye, said apparatus comprising:
    an applanation tonometer having a distal end that is movable toward the eye;
    a disposable module positioned at said distal end of said applanation tonometer, said module including a sensor carrier and a sensor connected to said sensor carrier, said sensor comprising:
        a contact surface for making contact with a surface portion of the eye, said contact surface including an outer non-compliant region and an inner compliant region fabricated as an impedance element that varies in impedance as said inner compliant region changes shape; and
        a region of conductive material electrically coupled to said impedance element of said compliant region and responsive to an external signal for energizing said impedance element so that the intraocular pressure may be determined; and
    an antenna positioned at said distal end of said applanation tonometer for transmitting the external signal for energizing said impedance element.

2. The apparatus of claim 1 wherein said sensor is comprised of silicon material.

3. The apparatus of claim 1 wherein said sensor is bonded to said sensor carrier.

4. The apparatus of claim 1 wherein said sensor is connected by spring means to said sensor carrier.

5. The apparatus of claim 1 wherein said sensor is comprised of a polymeric material.

6. The apparatus of claim 5 wherein said sensor comprises at least two layers of polymeric film bonded together.

7. The apparatus of claim 1 wherein said compliant region comprises a diaphragm that functions as one plate of a capacitive element, said diaphragm being separated by a dielectric region from another plate of said capacitive element, said diaphragm flexing closer to said other plate as said contact surface is pressed against the surface portion of the eye to change the capacitance of said capacitive element in proportion to the intraocular pressure of the eye.

8. The apparatus of claim 7 wherein said dielectric region comprises air.

9. The apparatus of claim 7 wherein said dielectric region comprises hydrogel.

10. The apparatus of claim 7 wherein said dielectric region comprises silicone.

11. The apparatus of claim 7 wherein said region of conductive material comprises an inductor coil that is electrically coupled to said capacitive element to form a resonant circuit, the external signal comprising an electromagnetic signal that varies in frequency to cause said resonant circuit to be energized and resonant at a frequency in proportion to the capacitance of said capacitive element so that the intraocular pressure may be determined.

12. The apparatus of claim 11 wherein said inductor coil is fabricated in said non-compliant region.

13. The apparatus of claim 11 wherein said inductor coil is formed by disposing conductive material in a predetermined pattern in a surface of said non-compliant region about said compliant region of said contact surface.

14. The apparatus of claim 11 wherein said inductor coil is fabricated on said inner compliant region.

15. The apparatus of claim 14 further comprising a second inductor coil formed underneath said diaphragm.

16. The apparatus of claim 1 further comprising a control unit for generating the external signal to measure a signal representative of intraocular pressure, said control unit being operatively coupled with said antenna.

17. The apparatus of claim 16 wherein said compliant region comprises a capacitive element that changes capacitance in proportion to its change in shape, said region of conductive material comprising an inductive coil electrically coupled to said capacitive element to form a resonant circuit.

18. The apparatus of claim 17 wherein said means for generating an external signal generates an electromagnetic signal that varies over a predetermined frequency range to cause said resonant circuit to resonate, said control unit including means for measuring the resonant frequency of said resonant circuit which is representative of the intraocular pressure of the eye.

19. The apparatus of claim 16 wherein said control unit includes a display for displaying the intraocular pressure measurements.

20. The apparatus of claim 16 wherein said control unit includes processing means for measuring signals representative of intraocular pressure at different times during a predetermined time interval, and a memory for storing the measured signals representative of the intraocular pressure measured at said different times.

21. The apparatus of claim 20 wherein said control unit includes means for processing the stored measured signals representative of intraocular pressure to determine a resultant intraocular pressure (IOP) measurement.

22. The apparatus of claim 21 wherein said control unit includes means for time marking each resultant IOP measurement with a measurement time and for storing said resultant IOP measurements with their corresponding measurement times in the memory.

23. The apparatus of claim 22 wherein said control unit includes means for transferring the stored resultant IOP measurements and their corresponding measurement times to another system.

24. The apparatus of claim 1 wherein said sensor further comprises a region of material responsive to a non-invasive external force to press said contact surface against the surface portion of the eye and cause said inner compliant region to change shape in proportion to the intraocular pressure.

25. The apparatus of claim 24 wherein said region of material responsive to a non-invasive external force comprises a magnetic material responsive to a magnetic field, the strength of said magnetic field determining the external force at which said contact surface is pressed against the surface portion of the eye.

26. The apparatus of claim 25 further comprising a control unit for generating a non-invasive force over a predetermined time interval and for generating said external signal to measure a signal representative of intraocular pressure.

27. The apparatus of claim 26 wherein said control unit includes means for generating a magnetic field as said non-invasive external force.

28. The apparatus of claim 27 wherein said control unit includes means for generating said external signal superimposed on said magnetic field.

29. A method for measuring intraocular pressure (IOP) of an eye, said method comprising the steps of:
providing an applanation tonometer with a distal end that is movable toward the eye;
positioning a disposable module at the distal end of the applanation tonometer, the module including a sensor carrier and a sensor connected to the carrier, the sensor having a compliant region that functions as an impedance element;
moving the distal end of the applanation tonometer via a non-invasive force which presses the complaint region against the surface portion of the eye in accordance with a predetermined force vs. time envelope, causing the compliant region to change shape and vary in impedance;
energizing the impedance element;
determining a representative pressure measurement each time the impedance element is energized; and
processing the representative pressure measurements to render a resultant IOP measurement.

30. The method of claim 29 wherein said step of energizing the impedance element is performed multiple times during the force vs. time envelope.

31. The method of claim 29 wherein said step of generating a non-invasive force includes the steps of:
generating a magnetic field in accordance with a magnetic field strength vs. time envelope; and
causing a permanent magnet region on the sensor to press the compliant region against the surface portion of the eye.

32. The method of claim 29 wherein said step of energizing the impedance element includes generating an electromagnetic signal that energizes the impedance element, the electromagnetic signal being superimposed on the magnetic field that causes the permanent magnet region on the sensor to press the compliant region against the surface portion of the eye.

33. The method of claim 29, further comprising the step of removing the disposable module from the distal end of the applanation tonometer.

34. The method of claim 29 wherein said step of energizing the impedance element includes the step of:
energizing an inductive region of the sensor that is connected to the impedance element which is a capacitive region to cause a circuit formed by the regions to resonate.

35. The method of claim 34 wherein said step of energizing an inductive region of the sensor includes transmitting an activation signal over an antenna.

36. The method of claim 34 wherein said step of energizing the impedance element includes generating an electromagnetic signal with a frequency that is swept through a frequency range over a predetermined time interval, the resonant frequency of the circuit falling within said frequency range.

37. The method of claim 36 wherein said step of determining includes the steps of determining the resonant frequency of the circuit each time the circuit is energized, the resonant frequencies sampled being representative of the IOP of the eye at different times.

38. The method of claim 37 wherein said step of processing includes processing the sampled data resonant frequencies to render a resultant IOP measurement.

39. The method of claim 38 further comprising the steps of:
time marking each resultant IOP measurement; and
storing each IOP measurement along with its corresponding measurement time.

40. The method of claim 39 further comprising the step of transmitting the stored IOP measurements and their corresponding measurement times to an external site.

41. The method of claim 40 wherein said steps of energizing, determining and processing are performed autonomously by a control unit.

42. The method of claim 41 further comprising the step of displaying the resultant IOP measurement on the control unit.

43. The method of claim 42 further comprising the step of displaying the resultant IOP measurement.

44. An apparatus for measuring intraocular pressure of an eye, said apparatus comprising:
an applanation tonometer having a distal end that is movable toward the eye; and
a disposable module positioned at said distal end of said applanation, tonometer, said module including a sensor carrier and a sensor connected to said sensor carrier , said sensor comprising:
a contact surface for making contact with a surface portion of the eye, said contact surface including an outer non-compliant region and an inner compliant region fabricated as an impedance element that varies in impedance as said inner compliant region changes shape, said inner compliant region comprising a diaphragm that functions as one plate of a capacitive element, said diaphragm being separated by a dielectric region from another plate of said capacitive element, said diaphragm flexing closer to said other plate as said contact surface is pressed against the surface portion of the eye to change the capacitance of said capacitive element in proportion to the intraocular pressure of the eye; and
a region of conductive material electrically coupled to said impedance element of said compliant region and responsive to an external signal for energizing said impedance element so that the intraocular pressure may be determined, said region of conductive material comprising an inductor coil, fabricated on said inner compliant region, that is electrically coupled to said capacitive element to form a resonant circuit, the external signal comprising an electromagnetic signal that varies in frequency to cause said resonant circuit to be energized and resonant at a frequency in proportion to the capacitance of said capacitive element so that the intraocular pressure may be determined.

45. An apparatus for measuring intraocular pressure of an eye, said apparatus comprising:
an applanation tonometer having a distal end that is movable toward the eye; and
a disposable module positioned at said distal end of said applanation tonometer, said module including a sensor carrier and a sensor connected to said sensor carrier, said sensor comprising:
a contact surface for making contact with a surface portion of the eye, said contact surface including an outer non-compliant region and an inner compliant region fabricated as an impedance element that varies in impedance as said inner compliant region changes shape; and
a region of conductive material electrically coupled to said impedance element of said compliant region and responsive to an external signal for energizing said impedance element so that the intraocular pressure may be determined; and
a region of magnetic material responsive a magnetic field as to produce a external non-invasive force that presses said contact surface against the surface portion of the eye and causes said inner compliant region to change shape in proportion to the intraocular pressure, the strength of said magnetic field determining the external force at which said contact surface is pressed against the surface portion of the eye.

46. An apparatus for measuring intraocular pressure of an eye, said apparatus comprising:
an applanation tonometer having a distal end that is movable toward the eye; and
a disposable module positioned at said distal end of said applanation tonometer, said module including a sensor carrier and a sensor connected to said sensor carrier via a spring means, said sensor comprising:
a contact surface for making contact with a surface portion of the eye, said contact surface including an outer non-compliant region and an inner compliant region fabricated as an impedance element that varies in impedance as said inner compliant region changes shape; and
a region of conductive material electrically coupled to said impedance element of said compliant region and responsive to an external signal for energizing said impedance element so that the intraocular pressure may be determined.

* * * * *